(12) United States Patent
Flasinski

(10) Patent No.: US 8,846,892 B2
(45) Date of Patent: Sep. 30, 2014

(54) CHIMERIC PLANT PROMOTERS AND THEIR USES IN PLANTS

(75) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 521 days.

(21) Appl. No.: 13/062,945

(22) PCT Filed: Sep. 25, 2009

(86) PCT No.: PCT/US2009/058462
§ 371 (c)(1),
(2), (4) Date: Jun. 28, 2011

(87) PCT Pub. No.: WO2010/036946
PCT Pub. Date: Apr. 1, 2010

(65) Prior Publication Data
US 2011/0252491 A1    Oct. 13, 2011

Related U.S. Application Data

(60) Provisional application No. 61/099,997, filed on Sep. 25, 2008.

(51) Int. Cl.
| C07H 21/04 | (2006.01) |
| C12N 5/10 | (2006.01) |
| C12N 5/14 | (2006.01) |
| A01H 5/00 | (2006.01) |
| C12N 15/82 | (2006.01) |

(52) U.S. Cl.
CPC .......... *C12N 15/8216* (2013.01); *C12N 15/823* (2013.01); *C12N 15/8275* (2013.01); *C12N 15/8223* (2013.01)
USPC ......... 536/24.1; 536/23.1; 800/278; 800/260; 800/298; 435/419

(58) Field of Classification Search
None
See application file for complete search history.

(56) References Cited

U.S. PATENT DOCUMENTS

| 6,555,673 B1 * | 4/2003 | Bowen et al. ................ 536/24.1 |
| 2007/0006335 A1 | 1/2007 | Cook et al. | |

FOREIGN PATENT DOCUMENTS

WO    WO 01/44457 A2  *  6/2001

OTHER PUBLICATIONS

Shinn et al., AC026875, 2000_Part 1.*
Shinn et al., AC026875, 2000_Part 2.*
Curie et al., Nucl Acids Res 19(6):1305-10 (1991).*
Potenza_In Vitro Cell Dev Biol Plant_40_1_2004.*
Tian_J Plant Physiol_162_1355_2005.*
Brander_BBA_1261_442_1995.*
Mandel_Plant Mol Biol_29_995_1995.*
Fincher_alignment_2001.*
Odell et al., "Identification of DNA sequences required for activity of the cauliflower mosaic virus 35S promoter," *Nature*, 313:810-812, 1985.
Cho et al., "Regulation of root hair initiation and expansin gene expression in arabidopsis," *The Plant Cell*, 14:3237-3253, 2002.
Piechulla et al., "Identification of tomato Lhc promoter regions necessary for circadian expression," *Plant Molecular Biology*, 38:655-662, 1998.
Welsch et al., "Structural and functional characterization of the phytoene synthase promoter from Arabidopsis thaliana," *Planta*, 216:523-534, 2003.
Database EMBL [Online], "Genomic sequence for Arabidopsis thaliana BAC T6D22 from chromosome I, complete sequence," retrieved from EBI accession No. EMBL:AC026875 Database accession No. AC028675, Nov. 4, 2011.
Database EMBL [Online], "Arabidopsis thaliana AT.I.24-1, AT.I.24-2, AT.I.24-3, AT.I.24-4, At.I.24-5, AT.I.24-6, AT.I.24-9, and AT.I.24-14 genes, partial cds, AT.I.24-7, ascorbate peroxidase (ATHAPX1), EF-1alpha-Al, -A2 and -A3 (EF-1-alpha) and AT.I.24-13 genes, complete cds," retrieved from EBI accession No. EMBL:U63815 Database accession No. U63815, Nov. 4, 2011.
Axelos et al., "The gene family encoding the Arabidopsis-thaliana translation elongation factor EF-1-alpha molecular cloning characterization and expression," *Molecular and General Genetics*, 219(1-2):106-112, 1989.
Curie et al., "Cis and trans-acting elements involved in the activation of Arabidopsis-thaliana Al gene encoding the translation elongation factor EF-1-alpha," *Nucleic Acids Research*, 19(6):1305-1310, 1991.
Curie et al., "The activation process of Arabidopsis-thaliana A1 gene encoding the translation elongation factor EF-1-alpha is conserved among angiosperms," *Plant Molecular Biology*, 18(6): 1083-1089, 1992.
Ni et al., "Strength and tissue specificity of chimeric promoters derived from the octopine and mannopine synthase genes," *Plant Journal*, 7(4):661-676, 1995.
Fang et al., "Multiple cis regulatory elements for maximal expression of the cauliflower mosaic virus 35S promoter in transgenic plants," *Plant Cell*, 1(1):141-150, 1989.
Kay et al., "Duplication of CaMV 35S promoter sequences creates a strong enhancer for plant genes," *Science*, 236(4806):1299-1302, 1987.
Kim et al., "A 20 nucleotide upstream element is essential for the nopaline synthase (nos) promoter activity," *Plant Molecular Biology*, 24:105-117, 1994.
Benfey et al., "The CaMV 35S enhancer contains at least two domains which can confer different developmental and tissue-specific expression patterns," *The EMBO Journal*, 8(8):2195-2202, 1989.

* cited by examiner

*Primary Examiner* — Medina A Ibrahim
*Assistant Examiner* — Russell Boggs
(74) *Attorney, Agent, or Firm* — Dentons US LLP; Carine M. Doyle, Esq.

(57) ABSTRACT

The present invention provides novel promoters for use in plants. Specifically, the present invention provides novel chimeric promoters comprising combinations of plant enhancer elements and plant promoters. The present invention also provides DNA constructs; transgenic cells, plants, and seeds containing these novel chimeric promoters; and methods for preparing and using the same.

18 Claims, 3 Drawing Sheets

US 8,846,892 B2

CHIMERIC PLANT PROMOTERS AND THEIR USES IN PLANTS

REFERENCE TO RELATED APPLICATIONS

This application claims priority to U.S. Provisional Application No. 61/099,997, filed on Sep. 25, 2008, which is incorporated herein by reference in its entirety.

INCORPORATION OF SEQUENCE LISTING

The Sequence Listing, which is a part of the present disclosure, includes a computer readable 52 KB file entitled "MONS226WO_ST25. txt" comprising nucleotide and/or amino acid sequences of the present invention submitted via EFS-Web. The subject matter of the Sequence Listing is incorporated herein by reference in its entirety.

FIELD OF THE INVENTION

The invention relates to the field of plant molecular biology and plant genetic engineering and DNA molecules useful for modulating gene expression in plants.

BACKGROUND

Promoters are genetic elements that regulate gene activity by modulating the transcription of an operably linked transcribable DNA molecule. Promoters may be defined as constitutive, i.e., generally always active, or by their temporal, spatial, developmental, tissue, environmental, physiological, pathological, cell cycle, and/or chemically responsive expression pattern, and any combination thereof, as well as by quantitative or qualitative indications. Optimal expression of a transgene in a plant can be achieved by using novel chimeric promoters.

SUMMARY OF THE INVENTION

The present invention provides novel chimeric promoters for use in plants. The present invention also provides DNA constructs comprising the chimeric promoters. The present invention also provides transgenic plant cells, plants, and seeds comprising the chimeric promoters operably linked to a transcribable DNA molecule. The present invention also provides methods of making and using the chimeric promoters, the DNA constructs comprising the chimeric promoters, and the transgenic plant cells, plants, and seeds comprising the chimeric promoters operably linked to a transcribable DNA molecule.

In a first embodiment there is provided a DNA molecule comprising a chimeric promoter comprising a first DNA sequence having promoter activity operably linked to a heterologous DNA sequence having enhancer activity. In certain embodiments, a chimeric promoter comprises a first DNA sequence selected from the group consisting of: i) a DNA sequence of SEQ ID NO: 2, 6, 12, 17, 21, 25, 27, 29, 33, 36, 39, 42, 48, 49 or 50; ii) a DNA sequence with at least about 95 percent sequence identity to SEQ ID NO: 2, 6, 12, 17, 21, 25, 27, 29, 33, 36, 39, 42, 48, 49 or 50 having promoter activity; and iii) a fragment of SEQ ID NO: 2, 6, 12, 17, 21, 25, 27, 29, 33, 36, 39, 42, 48, 49 or 50 having promoter activity. In a further embodiment, the first DNA sequence is operably linked to a heterologous DNA sequence selected from the group consisting of: i) a DNA sequence of SEQ ID NO: 1, 3, 4, 5, 7, 8, 10, 11, 13, 15, 16, 18, 19, 22, 23, 30, 31, 32, 34, 37, 38, 40, 43 or 44; ii) a DNA sequence with at least about 95 percent sequence identity to SEQ ID NO: 1, 3, 4, 5, 7, 8, 10, 11, 13, 15, 16, 18, 19, 22, 23, 30, 31, 32, 34, 37, 38, 40, 43 or 44 having enhancer activity; and iii) a fragment of SEQ ID NO: 1, 3, 4, 5, 7, 8, 10, 11, 13, 15, 16, 18, 19, 22, 23, 30, 31, 32, 34, 37, 38, 40, 43 or 44 having enhancer activity. In still a further embodiment, a chimeric promoter sequence is selected from the group consisting of a) a DNA sequence of SEQ ID NO: 9, SEQ ID NO: 14, SEQ ID NO: 20, SEQ ID NO: 26, SEQ ID NO: 35, SEQ ID NO: 41, SEQ ID NO: 45, SEQ ID NO: 46 or SEQ ID NO: 47; and b) a DNA sequence with at least about 95 percent sequence identity to SEQ ID NO: 9, SEQ ID NO: 14, SEQ ID NO: 20, SEQ ID NO: 26, SEQ ID NO: 35, SEQ ID NO: 41, SEQ ID NO: 45, SEQ ID NO: 46 or SEQ ID NO: 47.

In a further embodiment, a DNA molecule comprising a chimeric promoter described herein is operably linked to a transcribable DNA molecule, such as a gene of agronomic interest. Genes of agronomic interest include, but are not limited to, genes capable of providing herbicide resistance in plants or gene capable of providing plant pest control in plants.

In another embodiment there is a provided a stably transformed plant, plant cell or plant part comprising a DNA molecule according to the invention. Thus, in certain aspects, there is provided a transgenic plant or plant cell comprising a DNA molecule according to the invention. Such transgenic plants or plant cells may be dicotyledonous or monocotyledonous plants or cells thereof. For example, a transgenic plant or plant cell may be a tobacco, tomato, potato, soybean, cotton, canola, sunflower or alfalfa plant or plant cell. In still a further embodiment, there is provided a plant seed or progeny plant of a transgenic plant described herein wherein the seed or progeny plant comprises a DNA molecules according the invention.

In yet a further embodiment, a method of producing a progeny plant is provided comprising growing a transgenic plant comprising a DNA molecule described herein to a reproductive stage, and crossing the transgenic plant with another plant to produce a progeny plant.

In still yet a further embodiment, a method of providing a plant with a beneficial agronomic trait is provided comprising expressing in the plant a DNA molecule described herein, wherein the DNA molecule is operably linked to a transcribable DNA molecule capable of providing said beneficial agronomic trait. For example, a method of providing a plant with a beneficial agronomic trait may be used to provide a wheat, maize, rye, rice, corn, oat, barley, sorghum, millet, tobacco, tomato, potato, soybean, cotton, canola, sunflower and alfalfa, asparagus, avocado, banana, barley, beans, beet, blackberry, blueberry, broccoli, brussel sprouts, cabbage, canola, cantaloupe, carrot, cassava, cauliflower, celery, cherry, cilantro, cucumber, eggplant, honey dew, jicama, lettuce, leeks, melon, onion, papaya, parsley, pea, peanut, pepper, plum, pomegranate, poplar, potato, pumpkin, quince, radish, raspberry, spinach, squash, strawberry, sugarbeet, sugarcane, sweet potato, tobacco, tomato, watermelon, yams, or zucchini plant with a beneficial agronomic trait. Some beneficial agronomic traits include, but are not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production and biofuel production.

BRIEF DESCRIPTION OF THE SEQUENCE LISTING

Figure 1:
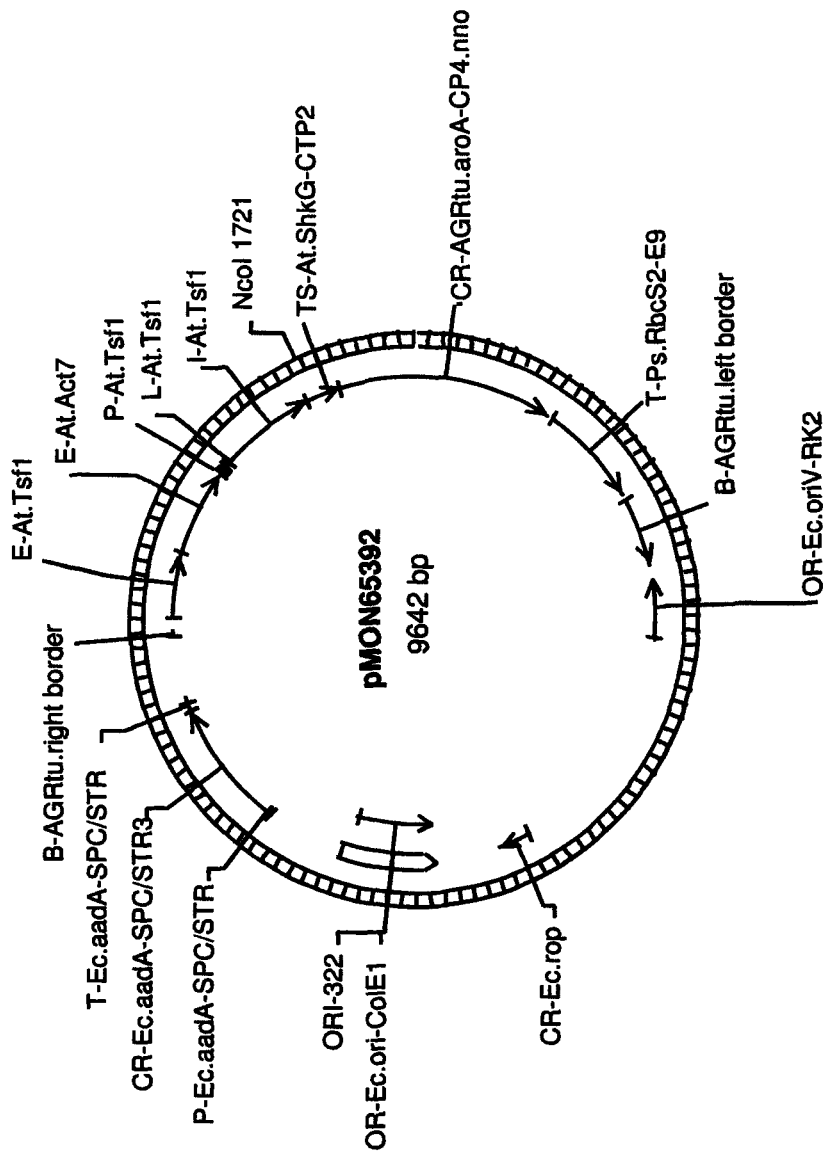
FIG. 1 illustrates the pMON65392 DNA construct, comprising a right border region from *Agrobacterium tumefaciens* (B-AGRtu.right border), a chimeric promoter comprising an enhancer segment (E-At.Tsf1) from *Arabidopsis thaliana* elongation factor 1-alpha promoter linked to an enhancer segment from *Arabidopsis thaliana* Actin 7 gene promoter (E-At.Act7) linked to segment of the *Arabidopsis thaliana* elongation factor 1-alpha promoter (P-ALTsf1), linked to a leader segment from At.Tsf1 (L-ALTsf1), linked to a intron segment from At.Tsf1 (I-ALTsf1), linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4. nno), linked to a 3' termination region from pea rubisco small subunit (T-Ps.Rbc.S2-E9), linked to a left border region from *Agrobacterium tumefaciens* (B-AGRtu.left border).
Figure 2:
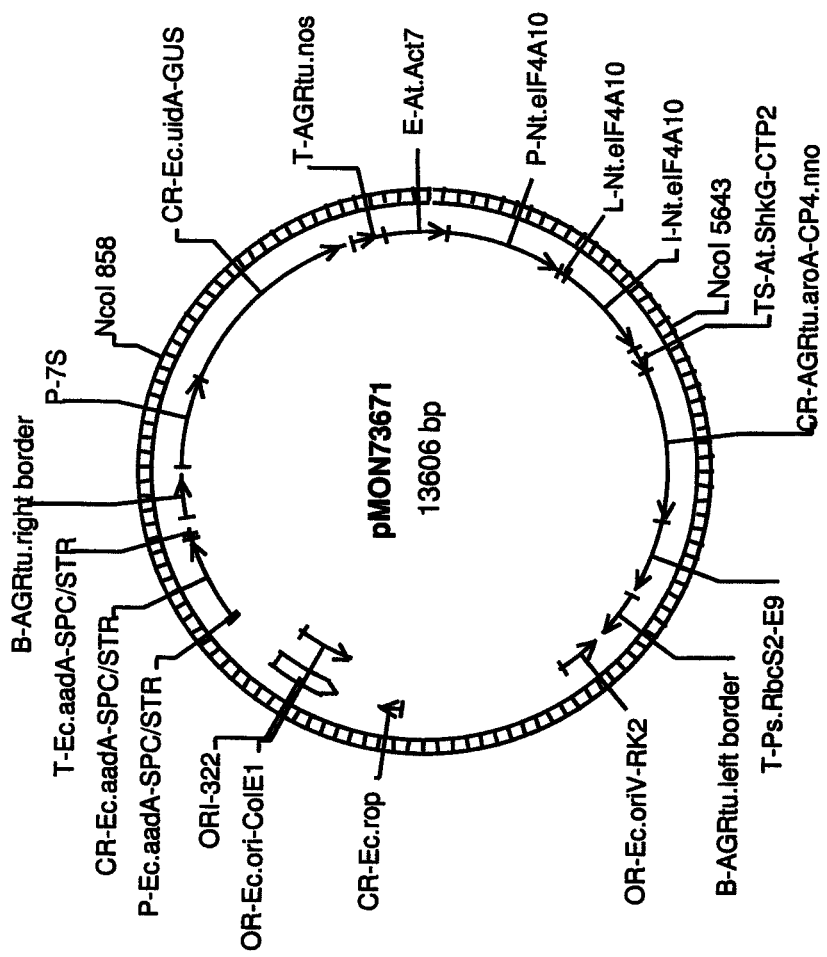
FIG. 2 illustrates the pMON73671 DNA construct, comprising a right border region from *Agrobacterium tumefaciens* (B-AGRtu.right border), a chimeric promoter comprising an enhancer segment (E-At.Act7) from *Arabidopsis thaliana* Act7 promoter linked a promoter segment from *Nicotiana tabacum* initiation factor 4A10 (P-Nt.e1F4A10) linked to a leader segment from *Nicotiana tabacum* initiation factor 4A10 (L-Nt.e1F4A10) linked to an intron segment from *Nicotiana tabacum* initiation factor 4A10 (I-Nt.elf4A10) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).
Figure 3:
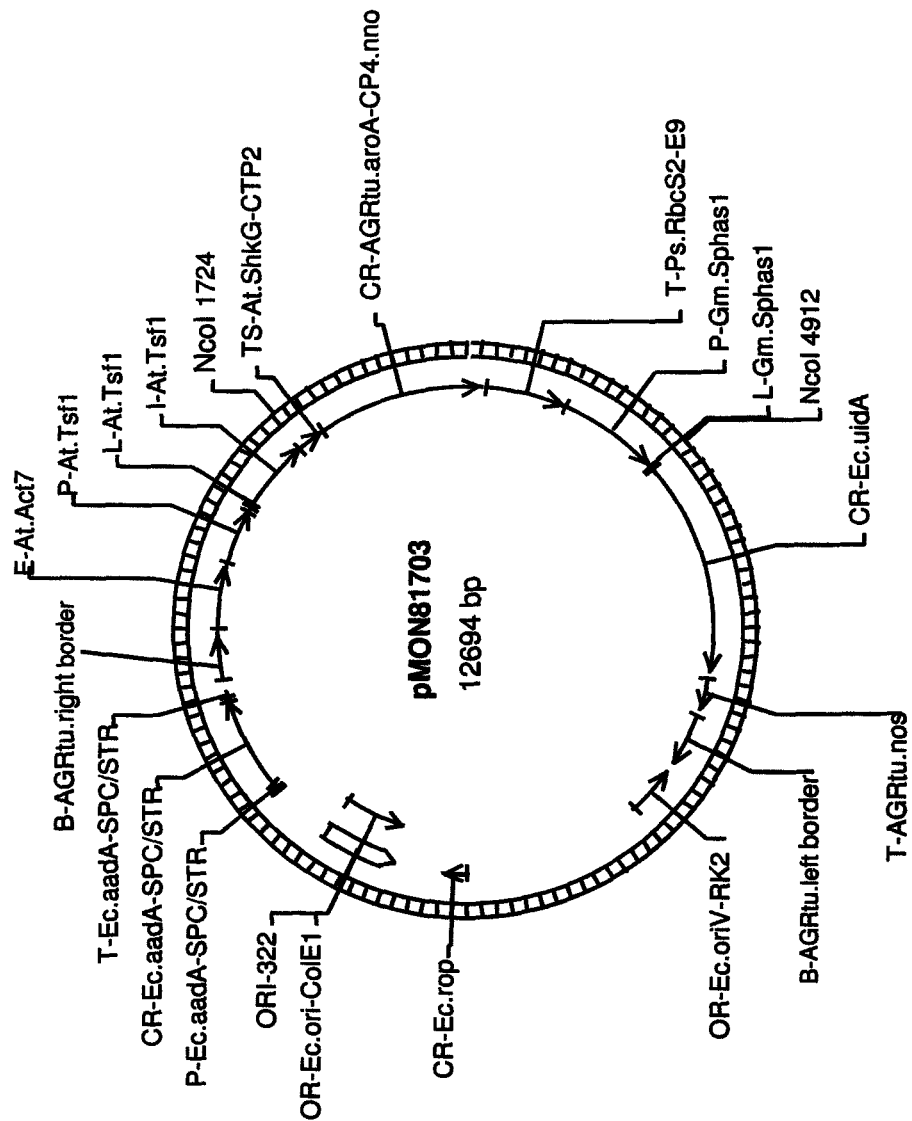
FIG. 3 illustrates the pMON81703 DNA construct, comprising a right border region from *Agrobacterium tumefaciens* (B-AGRtu.right border), a chimeric promoter comprising an enhancer segment (E-At.Act7) from *Arabidopsis thaliana* Act7 promoter linked, linked to a segment of the *Arabidopsis thaliana* elongation factor 1-alpha promoter (P-At.Tsf1), linked to a leader segment from At.Tsf1 (L-At.Tsf1), linked to a intron segment from At.Tsf1 (I-At.Tsf1), linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 1 is the DNA sequence of the transcriptional regulatory element, EXP-At.Tsf1 derived from the *Arabidopsis thaliana* elongation factor 1α gene.

SEQ ID NO: 2 is the DNA sequence of the promoter element, P-At.Tsf1-1:1:6 derived from the *Arabidopsis thaliana* elongation factor 1α gene.

SEQ ID NO: 3 is the DNA sequence of the leader element, L-At.Tsf1-1:1:1 derived from the *Arabidopsis thaliana* elongation factor 1α gene.

SEQ ID NO: 4 is the DNA sequence of the intron element, I-At.Tsf1-1:1:8 derived from the *Arabidopsis thaliana* elongation factor 1α gene.

SEQ ID NO: 5 is the DNA sequence of the transcriptional regulatory element, EXP-At.Act7 derived from the *Arabidopsis thaliana* actin 7 gene.

SEQ ID NO: 6 is the DNA sequence of the promoter element, P-At.Act7-1:1:3 derived from the *Arabidopsis thaliana* actin 7 gene.

SEQ ID NO: 7 is the DNA sequence of the leader element, L-At.Act7-1:1:2 derived from the *Arabidopsis thaliana* actin 7 gene.

SEQ ID NO: 8 is the DNA sequence of the intron element, I-At.Act7-1:1:2 derived from the *Arabidopsis thaliana* actin 7 gene.

SEQ ID NO: 9 is the DNA sequence of the chimeric transcriptional regulatory element, EXP-At.Act7/At.Tsf1/At.Tsf1.

SEQ ID NO: 10 is the DNA sequence of the enhancer element, E-At.Act7-1:1:1 derived from the *Arabidopsis thaliana* actin 7 gene.

SEQ ID NO: 11 is the DNA sequence of the enhancer element, E-At.Tsf1-1:1:1 derived from the *Arabidopsis thaliana* elongation factor 1a gene.

SEQ ID NO: 12 is the DNA sequence of the promoter element, P-At.Tsf1-1:1:11 derived from the *Arabidopsis thaliana* elongation factor 1α gene.

SEQ ID NO: 13 is the DNA sequence of the intron element, I-At.Tsf1-1:1:11 derived from the *Arabidopsis thaliana* elongation factor 1α gene.

SEQ ID NO: 14 is the DNA sequence of the chimeric transcriptional regulatory element, EXP-At.Tsf1/At.Act7/At.Tsf1.

SEQ ID NO: 15 is the DNA sequence of the enhancer element, E-At.Act7-1:1:2 derived from the *Arabidopsis thaliana* actin 7 gene.

SEQ ID NO: 16 is the DNA sequence of the regulatory element, EXP-At.EF1beta derived from the *Arabidopsis thaliana* elongation factor-1 beta gene.

SEQ ID NO: 17 is the DNA sequence of the promoter element, P-At.EF1beta-0:0:1 derived from the *Arabidopsis thaliana* elongation factor-1 beta gene.

SEQ ID NO: 18 is the DNA sequence of the leader element, L-At.EF1beta-0:0:2 derived from the *Arabidopsis thaliana* elongation factor-1 beta gene.

SEQ ID NO: 19 is the DNA sequence of the intron element, I-At.EF1beta-0:0:1 derived from the *Arabidopsis thaliana* elongation factor-1 beta gene.

SEQ ID NO: 20 is the DNA sequence of the chimeric transcriptional regulatory element, EXP-ALTsf1/Nt.e1F-4A10.

SEQ ID NO: 21 is the DNA sequence of the promoter element, P-Nt.eIF-4A10-0:0:2 derived from the *Nicotiana tabacum* initiation factor 4A10 gene.

SEQ ID NO: 22 is the DNA sequence of the leader element, L-Nt.eIF4A10-1:1:1 derived from the *Nicotiana tabacum* initiation factor 4A10 gene.

SEQ ID NO: 23 is the DNA sequence of the intron element, I-Nt.eIF4A10-0:0:2 derived from the *Nicotiana tabacum* initiation factor 4A10 gene.

SEQ ID NO: 24 is the DNA sequence of the chimeric transcriptional regulatory element, EXP-At.Tsf1/At.EF1beta.

SEQ ID NO: 25 is the DNA sequence of the promoter element, P-At.EF1beta-0:0:2 derived from the *Arabidopsis thaliana* elongation factor-1 beta gene.

SEQ ID NO: 26 is the DNA sequence of the chimeric transcriptional regulatory element, EXP-At.Tsf1/At.Act7.

SEQ ID NO: 27 is the DNA sequence of the promoter element, P-At.Act7-1:1:5 derived from the *Arabidopsis thaliana* actin 7 gene.

SEQ ID NO: 28 is the DNA sequence of the chimeric transcriptional regulatory element, EXP-At.Tsf1/At.enr-A.

SEQ ID NO: 29 is the DNA sequence of the promoter element, P-At.enr-A-0:0:4 derived from the *Arabidopsis thaliana* enoyl-ACP reductase gene.

SEQ ID NO: 30 is the DNA sequence of the leader element, L-At.enr-A-0:0:2 derived from the *Arabidopsis thaliana* enoyl-ACP reductase gene.

SEQ ID NO: 31 is the DNA sequence of the intron element, I-At.enr-A-0:0:1 derived from the *Arabidopsis thaliana* enoyl-ACP reductase gene.

SEQ ID NO: 32 is the DNA sequence of the transcriptional regulatory element, EXP-Nt.eIF4A10 derived from the *Nicotiana tabacum* initiation factor 4A10 gene.

SEQ ID NO: 33 is the DNA sequence of the promoter element, P-Nt.eIF4A10-1:1:1 derived from the *Nicotiana tabacum* initiation factor 4A10 gene.

SEQ ID NO: 34 is the DNA sequence of the intron element, I-Nt.eIF4A10-1:1:1 derived from the *Nicotiana tabacum* initiation factor 4A10 gene.

SEQ ID NO: 35 is the DNA sequence of the chimeric transcriptional regulatory element, EXP-At.Act7/Nt.eIF4A10.

SEQ ID NO: 36 is the DNA sequence of the promoter element, P-Nt.eIF4A10-1:1:5 derived from the *Nicotiana tabacum* initiation factor 4A10 gene.

SEQ ID NO: 37 is the DNA sequence of the leader element, L-Nt.eIF4A10-1:1:2 derived from the *Nicotiana tabacum* initiation factor 4A10 gene.

SEQ ID NO: 38 is the DNA sequence of the chimeric transcriptional regulatory element, EXP-FMV/Ph.DnaK.

SEQ ID NO: 39 is the DNA sequence of the promoter element, P-FMV.35S-1:1:3 derived from the Figwort mosaic virus genome.

SEQ ID NO: 40 is the DNA sequence of the leader element, L-Ph.DnaK-1:1:2 derived from the *Petunia hybrida* Hsp70 heat shock protein gene.

SEQ ID NO: 41 is the DNA sequence of the chimeric transcriptional regulatory element, EXP-At.Act7/At.Tsf1

SEQ ID NO: 42 is the DNA sequence of the promoter element, P-At.Tsf1-1:1:7 derived from the derived from the *Arabidopsis thaliana* elongation factor 1α gene.

SEQ ID NO: 43 is the DNA sequence of the 3' UTR element, T-Ps.RbcS2-E9-1:1:3 derived from the *Pisum sativum* ribulose-1,5-bisphosphate carboxylase small subunit (RbcS2) E9 gene.

SEQ ID NO: 44 is the DNA sequence of the 3' UTR element, T-AGRtu.nos-1:1:13 derived from the *Agrobacterium tumefaciens* nopaline synthase gene.

SEQ ID NO: 45 is the DNA sequence of the chimeric AtTsf1/AtAct7 promoter.

SEQ ID NO: 46 is the DNA sequence of the chimeric AtAct7/NteIF4A10 promoter.

SEQ ID NO: 47 is the DNA sequence of the chimeric AtAct7/AtTsf1.

SEQ ID NO: 48 is the DNA sequence of the AtAct7 promoter.

SEQ ID NO: 49 is the DNA sequence of the AtTsf1 promoter.

SEQ ID NO: 50 is the DNA sequence of the NteIF4A10 promoter.

SEQ ID NO: 51 is the DNA sequence of the AtTsf1 intron.

SEQ ID NO: 52 is the DNA sequence of the NteIF4A10 intron.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides novel chimeric promoters. The design, construction, and use of these DNA molecules is one object of this invention. The invention also includes DNA constructs comprising the chimeric promoters; transgenic plant cells, plants, and seeds comprising the chimeric promoters operably linked to a transcribable DNA molecule; and methods of making and using the chimeric promoters, the DNA constructs comprising the chimeric promoters, and the transgenic plant cells, plants, and seeds comprising the chimeric promoters.

DNA Molecules

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native state. In one embodiment, the term "isolated" is also used herein in reference to a DNA molecule that is at least partially separated from nucleic acids which normally flank the DNA molecule in its native state. Thus, DNA molecules fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein "sequence identity" refers to the extent to which two optimally aligned polynucleotide or polypeptide sequences are identical throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *Journal of Molecular Biology,* 48:443-453 (1970)) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics,* 2:482-489, 1981, Smith et al., *Nucleic Acids Research,* 11:2205-2220 (1983)). The percent identity is most preferably determined using the "Best Fit" program.

Useful methods known to those of skill in the art for determining sequence identity are also disclosed in *Guide to Huge Computers*, Martin J. Bishop, ed., Academic Press, San Diego (1994) and Carillo, H., and Lipton, D., *Applied Math.,* 48:1073 (1988). More particularly, preferred computer programs for determining sequence identity include the Basic Local Alignment Search Tool (BLAST) programs, which are publicly available from National Center Biotechnology Information (NCBI) at the National Library of Medicine, National Institute of Health, Bethesda, Md. 20894 (see also, *BLAST Manual*, Altschul et al., NCBI, NLM, NIH and Altschul et al., *Journal of Molecular Biology,* 215:403-410 (1990)). For polynucleotide sequence BLASTN can be used to determine sequence identity, and version 2.0 or higher of BLAST programs allows the introduction of gaps (deletions and insertions) into alignments. In certain aspects, a DNA molecule of the invention is at least about 70, 80, 85, 90, 95, 99 or 99.5 percent identical to a polynucleotide sequence selected from SEQ ID NO: 9, 14, 20, 24, 26, 28, 35, 41 or 45-47. Thus, one embodiment of the invention is a DNA molecule that has at least about 95 percent sequence identity with a polynucleotide sequence provided as SEQ ID NO: SEQ ID NO: 9, 14, 20, 24, 26, 28, 35, 41 or 45-47.

Promoters

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules.

Promoters may be characterized by their gene expression pattern, i.e., as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable DNA molecule.

As used herein, a "gene expression pattern" is any pattern of gene expression. The term "gene expression" refers to the transcription of a transcribable DNA molecule into a transcribed RNA molecule. Gene expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" refers to the translation of a transcribed RNA molecule into a protein molecule. Protein expression may be characterized by its temporal, spatial, developmental, or morphological qualities as well as by quantitative or qualitative indications.

As used herein, the term "gene regulatory activity" refers to the ability to affect the expression pattern of an operably linked transcribable DNA molecule by affecting the transcription and/or translation of that DNA molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

As used herein, the term "regulatory element" refers to a DNA molecule having gene regulatory activity, i.e., one that has the ability to affect the transcription and/or translation of an operably linked transcribable DNA molecule. Regulatory elements such as promoters, leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

A promoter may comprise fragments that have independent promoter activity or enhancer activity. Promoter fragments may be useful alone or in combination with other promoters and promoter fragments, such as in constructing chimeric promoters. Fragments of a promoter comprise at least about 50, 95, 150, 250, 500, and 750 contiguous nucleotides of the DNA sequence of the promoter molecule. For example, a promoter sequence may comprise SEQ ID NO: 2, 6, 12, 17, 21, 25, 27, 29, 33, 36, 39, 42, 48, 49 and 50 or a fragment thereof comprising at least about 50, 95, 150, 250, 500, and 750 contiguous nucleotides having promoter activity.

A promoter or promoter fragment may also be analyzed for the presence of known promoter elements, i.e., DNA sequence characteristics, such as a TATA-box and other known transcription factor binding site motifs. Identification of such known promoter elements may be used by one of skill in the art to design modified versions of the promoter having a similar expression pattern to the original promoter. Such modified versions of the promoter may be a shorter or truncated version of the original promoter and/or a variant version of the sequence of the original promoter, such as one with different restriction enzyme sites, internal deletions, and/or internal insertions. Such modified versions would usually have the same or similar expression pattern of the original promoter. Production of modified versions of the chimeric promoters of the present invention is well within the ordinary skill of the art and is encompassed within the scope of the present invention.

As used herein, the term "enhancer activity" refers to the capability of a polynucleotide sequence to increase expression of a transcribable polynucleotide, when operably linked to a promoter and transcribable polynucleotide. Thus, polynucleotide molecules having enhancer activity include, but are not limited to leader sequences, introns, transcriptional enhancer elements and, in some cases, molecules comprising 3' UTR sequences. Methods for determining whether a polynucleotide molecule comprises enhancer activity are well know in the art and described in detail below.

As used herein, the term "enhancer" or "enhancer element" refers to a cis-acting transcriptional regulatory element, a.k.a. cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the present invention.

DNA molecules comprising enhancer activity include but are not limited to molecules having a sequence of SEQ ID NO: 1, 3, 4, 5, 7, 8, 10, 11, 13, 15, 16, 18, 19, 22, 23, 30, 31, 32, 34, 37, 38, 40, 43 or 44 or a fragment thereof having enhancer activity. Fragments of DNA molecules comprising enhancer activity such as fragments of at least about 50, 95, 150, 250, 500, and 750 contiguous nucleotides of the DNA sequence may also be used as described herein.

As used herein, the term "chimeric" refers to a first DNA molecule fused to a second DNA molecule to produce a single chimeric DNA molecule. As used herein, the term "chimeric promoter" refers to a promoter produced through such manipulation of DNA molecules. A chimeric promoter may combine one or more promoter fragments, such as enhancer elements that can confer or modulate gene expression, fused to a heterologous second promoter or promoter fragment with its own partial or complete regulatory elements. Thus, the design, construction, and use of chimeric promoters according to the methods disclosed herein for modulating the expression of operably linked transcribable DNA molecules are encompassed by the present invention.

As used herein, a "plant promoter" is a promoter isolated from a plant. Plant promoters useful in practicing the present invention are provided as SEQ ID NO: 9, 14, 20, 24, 26, 28, 35, 41 or 45-47. Any of these plant promoters or fragments thereof can be combined with one or more of the other plant promoters or fragments thereof to create a chimeric promoter molecule of the present invention. If desired, the chimeric promoter can be analyzed in transformed plant cells or plants as described herein to characterize the expression pattern of the chimeric promoter. Such characterization may be useful to select a chimeric promoter that provides a desirable expression pattern for a gene of agronomic interest.

In certain embodiments a chimeric promoter of the invention is defined as a promoter capable of conferring herbicide tolerance in vegetative and reproduction plant tissues when operably linked to a herbicide tolerance gene and transformed into a plant. For example, a chimeric promoter may be defined as capable of confer glyphosate tolerance to vegetative and reproductive tissues of a transgenic plant transformed with a construct comprising the chimeric promoter operably linked to a glyphosate tolerance gene. In certain aspects, a chimeric, promoter is capable of conferring vegetative and reproductive glyphosate tolerant to a transgenic plant at an application rate of about 24, 52, 96, or 124 oz/Acre of a glyphosate composition (e.g., Roundup® Ultra or Roundup UltraMax II®). For example, a chimeric promoter may be defined as capable of conferring about 5%, 10%, 15%, 25%, 30%, 35%, 40%, 45%, 50%, 55%, 60%, 65% or more reproductive tolerance to glyphosate in a transgenic plant.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked. As used herein, the term "vector" means any recombinant polynucleotide construct that may be used for the purpose of transformation, i.e., the introduction of heterologous DNA into a host cell.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium tumefaciens* cells, permit the integration of the T-DNA into the genome of a plant cell (see, for example, U.S. Pat. No. 6,603,061, hereby incorporated by reference in its entirety). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404; however, other strains known to those skilled in the art of plant transformation can function in the present invention.

Methods are known in the art for assembling and introducing constructs into a cell in such a manner that the transcribable DNA molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, 3$^{rd}$ edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011, all of which are hereby incorporated by reference in their entirety. These types of vectors have also been reviewed in the scientific literature (see, for example, Rodriguez et al., *Vectors: A Survey of Molecular Cloning Vectors and Their Uses*, Butterworths, Boston, (1988) and Glick et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers et al., *Methods in Enzymology*, 153: 253-277 (1987)). Other recombinant vectors useful for plant transformation, including the pCaMVCN transfer control vector, have also been described in the scientific literature (see, for example, Fromm et al., *Proc. Natl. Acad. Sci. USA*, 82: 5824-5828 (1985)).

Various regulatory elements may be included in a construct. Any such regulatory elements may be provided in combination with other regulatory elements. Such combinations can be designed or modified to produce desirable regulatory features. Constructs of the present invention would typically comprise one or more regulatory elements operably linked to a transcribable DNA molecule operably linked to a 3' transcription termination molecule.

As used herein, the term "leader" refers to a DNA molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A leader can be used as a 5' regulatory element for modulating expression of an operably linked transcribable DNA molecule. For example, non-translated 5' leaders derived from heat shock protein genes have been demonstrated to enhance gene expression in plants (see, for example, U.S. Pat. Nos. 5,659,122 and 5,362,865, all of which are hereby incorporated by reference). Chimeric promoter molecules of the present invention may optionally comprise a native leader linked to the plant promoter segment for which it is naturally found. This molecule may be replaced with a heterologous leader.

As used herein, the term "intron" refers to a DNA molecule that may be isolated or identified from the genomic copy of a gene and may be defined generally as a region spliced out during mRNA processing prior to translation. Alternately, introns may be synthetically produced or manipulated DNA elements. Introns may themselves contain elements such as cis-elements or enhancer elements that effect the transcription of operably linked genes. An intron may be used as a regulatory element for modulating expression of an operably linked transcribable DNA molecule. A construct may comprise introns. The introns may or may not be heterologous with respect to the transcribable DNA molecule sequence. The transcribable DNA molecule sequence in the recombinant vector may comprise introns. The introns may be heterologous with respect to the transcribable DNA molecule sequence. Examples of introns include the rice actin intron (U.S. Pat. No. 5,641,876, hereby incorporated by reference) and the corn HSP70 intron (U.S. Pat. No. 5,859,347, hereby incorporated by reference).

As used herein, the term "3' transcription termination molecule" or "3' region" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' transcription termination molecule may be operably linked to and located downstream of a transcribable DNA molecule. A 3' transcription termination molecule may include polynucleotides that provide a polyadenylation signal and other regulatory signals capable of affecting transcription, mRNA processing or gene expression. PolyA tails are thought to function in mRNA stability and in initiation of translation. Examples of 3' transcription termination molecules are the nopaline synthase 3' region (nos 3') (see, Fraley et al., *Proc. Natl. Acad. Sci. USA*, 80: 4803-4807 (1983)), wheat hsp17 3' region (T-Ta.Hsp17), pea rubisco small subunit 3' region (T-Ps.RbcS2:E9), cotton E6 3' region (U.S. Pat. No. 6,096,950, hereby incorporated by reference), 3' regions disclosed in WO0011200A2, hereby incorporated by reference), and other 3' regions known in the art that can be used in combination with a transcribable DNA molecule, such as the coixin terminator (U.S. Pat. No. 6,635,806, hereby incorporated by reference).

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925, both of which are hereby incorporated by reference. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133, hereby incorporated by reference. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.*, 210:437-442 (1987)) or the *Petunia hybrida* EPSPS CTP (CTP4) (della-Cioppa et al., *Proc. Natl. Acad. Sci. USA*, 83:6873-6877 (1986)) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art (see, for example U.S. Pat. Nos. 5,627,061; 5,633,435; and 5,312,910 and EP 0218571; EP 189707; EP 508909; and EP 924299, all of which are hereby incorporated by reference).

Transcribable DNA Molecules

As used herein, the term "transcribable DNA molecule" refers to any DNA molecule capable of being transcribed into a RNA molecule, including, but not limited to, those having protein coding sequences and sequences useful for gene suppression. A "transgene" comprises a transcribable DNA molecule heterologous to a host cell.

A promoter of the present invention may be operably linked to a transcribable DNA molecule that is heterologous with respect to the promoter molecule. The term "heterologous" refers to the relationship between two or more polynucleotide molecules that are derived from different sources. For example, a promoter is heterologous with respect to a transcribable DNA molecule if such a combination is not normally found in nature. In addition, a particular molecule may be "heterologous" with respect to the cell or organism into which it is inserted (i.e., does not naturally occur in that particular cell or organism).

The transcribable DNA molecule may generally be any DNA molecule for which expression of an RNA transcript is desired. Such expression of an RNA transcript may result in translation of the resulting mRNA molecule and thus protein expression. Alternatively, a transcribable DNA molecule may be designed to ultimately cause decreased expression of a specific gene or protein. This may be accomplished by using a transcribable DNA molecule that is oriented in the antisense direction. One of ordinary skill in the art is familiar with using such antisense technology. Briefly, as the antisense transcribable DNA molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a chimeric promoter of the present invention, such as those provided as SEQ ID NO: 45-47, operably linked to a transcribable DNA molecule so as to modulate transcription of the transcribable DNA molecule at a desired level or in a desired pattern upon introduction of said construct into a plant cell. In one embodiment, the transcribable DNA molecule comprises a protein-coding region of a gene, and the chimeric promoter affects the transcription of an RNA molecule that is translated and expressed as a protein product. In another embodiment, the transcribable DNA molecule comprises an antisense region of a gene, and the chimeric promoter affects the transcription of an antisense RNA molecule or other similar inhibitory RNA molecule in order to inhibit expression of a specific RNA molecule of interest in a target host cell.

Genes of Agronomic Interest

Transcribable DNA molecules may be genes of agronomic interest. As used herein, the term "gene of agronomic interest" refers to a transcribable DNA molecule that when expressed in a particular plant tissue, cell, or cell type provides a desirable characteristic associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or dsRNA molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a chimeric promoter of the present invention is incorporated into a construct such that the chimeric promoter is operably linked to a transcribable DNA molecule that is a gene of agronomic interest. The expression of the gene of agronomic interest is desirable in order to confer an agronomically beneficial trait. A beneficial agronomic trait may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175, all of which are hereby incorporated by reference), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837, all of which are hereby incorporated by reference), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241, all of which are hereby incorporated by reference), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962, all of which are hereby incorporated by reference), virus resistance (U.S. Pat. Nos.

6,617,496; 6,608,241; 6,015,940; 6,013,864; 5,850,023; and 5,304,730, all of which are hereby incorporated by reference), nematode resistance (U.S. Pat. No. 6,228,992, which is hereby incorporated by reference), bacterial disease resistance (U.S. Pat. No. 5,516,671, which is hereby incorporated by reference), plant growth and development (U.S. Pat. Nos. 6,723,897 and 6,518,488, both of which are hereby incorporated by reference), starch production (U.S. Pat. Nos. 6,538,181; 6,538,179; 6,538,178; 5,750,876; 6,476,295, all of which are hereby incorporated by reference), modified oils production (U.S. Pat. Nos. 6,444,876; 6,426,447; and 6,380,462, all of which are hereby incorporated by reference), high oil production (U.S. Pat. Nos. 6,495,739; 5,608,149; 6,483,008; and 6,476,295, all of which are hereby incorporated by reference), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018, all of which are hereby incorporated by reference), high protein production (U.S. Pat. No. 6,380,466, which is hereby incorporated by reference), fruit ripening (U.S. Pat. No. 5,512,466, which is hereby incorporated by reference), enhanced animal and human nutrition (U.S. Pat. Nos. 6,723,837; 6,653,530; 6,5412,59; 5,985,605; and 6,171,640, all of which are hereby incorporated by reference), biopolymers (U.S. Pat. Nos. RE37,543; 6,228,623; and 5,958,745, and 6,946,588, all of which are hereby incorporated by reference), environmental stress resistance (U.S. Pat. No. 6,072,103, which is hereby incorporated by reference), pharmaceutical peptides and secretable peptides (U.S. Pat. Nos. 6,812,379; 6,774,283; 6,140,075; and 6,080,560, all of which are hereby incorporated by reference), improved processing traits (U.S. Pat. No. 6,476,295, which is hereby incorporated by reference), improved digestibility (U.S. Pat. No. 6,531,648, which is hereby incorporated by reference) low raffinose (U.S. Pat. No. 6,166,292, which is hereby incorporated by reference), industrial enzyme production (U.S. Pat. No. 5,543,576, which is hereby incorporated by reference), improved flavor (U.S. Pat. No. 6,011,199, which is hereby incorporated by reference), nitrogen fixation (U.S. Pat. No. 5,229,114, which is hereby incorporated by reference), hybrid seed production (U.S. Pat. No. 5,689,041, which is hereby incorporated by reference), fiber production (U.S. Pat. Nos. 6,576,818; 6,271,443; 5,981,834; and 5,869,720, all of which are hereby incorporated by reference) and biofuel production (U.S. Pat. No. 5,998,700, which is hereby incorporated by reference).

Alternatively, a gene of agronomic interest can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable DNA molecule that encodes a transcribed RNA molecule that affects an agronomically important phenotype or morphology change of interest may be useful for the practice of the present invention. Methods are known in the art for constructing and introducing constructs into a cell in such a manner that the transcribable DNA molecule is transcribed into a molecule that is capable of causing gene suppression. For example, posttranscriptional gene suppression using a construct with an antisense oriented transcribable DNA molecule to regulate gene expression in plant cells is disclosed in U.S. Pat. Nos. 5,107,065 and 5,759,829, both of which are hereby incorporated by reference, and posttranscriptional gene suppression using a construct with a sense-oriented transcribable DNA molecule to regulate gene expression in plants is disclosed in U.S. Pat. Nos. 5,283,184 and 5,231,020, both of which are hereby incorporated by reference. Expression of a transcribable polynucleotide in a plant cell can also be used to suppress plant pests feeding on the plant cell, for example, compositions isolated from coleopteran pests (U.S. Patent Publication No. US20070124836, which is hereby incorporated by reference) and compositions isolated from nematode pests (U.S. Patent Publication No. US20070250947, which is hereby incorporated by reference). Plant pests include, but are not limited to arthropod pests, nematode pests, and fungal or microbial pests. Exemplary transcribable DNA molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable DNA molecule whose expression, or lack thereof, can be screened for or scored in some way. Marker genes for use in the practice of the present invention include, but are not limited to transcribable DNA molecules encoding β-glucuronidase (GUS described in U.S. Pat. No. 5,599,670, which is hereby incorporated by reference), green fluorescent protein and variants thereof (GFP described in U.S. Pat. Nos. 5,491,084 and 6,146,826, both of which are hereby incorporated by reference), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable DNA molecules encoding proteins involved in herbicide tolerance are known in the art, and include, but are not limited to, a transcribable DNA molecule encoding 5-enolpyruvylshikimate-3-phosphate synthase (EPSPS for glyphos ate tolerance described in U.S. Pat. Nos. 5,627,061; 5,633,435; 6,040,497; and 5,094,945, all of which are hereby incorporated by reference); a transcribable DNA molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879, all of which are hereby incorporated by reference); a transcribable DNA molecule encoding bromoxynil nitrilase (Bxn for Bromoxynil tolerance described in U.S. Pat. No. 4,810,648, which is hereby incorporated by reference); a transcribable DNA molecule encoding phytoene desaturase (crtI) described in Misawa et al., *Plant Journal*, 4:833-840 (1993) and Misawa et al., *Plant Journal*, 6:481-489 (1994) for norflurazon tolerance; a transcribable DNA molecule encoding acetohydroxyacid synthase (AHAS, aka ALS) described in Sathasiivan et al., *Nucl. Acids Res.*, 18:2188-2193 (1990) for tolerance to sulfonylurea herbicides; and the bar gene described in DeBlock et al., *EMBO Journal*, 6:2513-2519 (1987) for glufosinate and bialaphos tolerance. The chimeric promoter molecules of the present invention can express linked transcribable DNA molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art.

Cell Transformation

The invention is also directed to a method of producing transformed cells and plants which comprise a chimeric promoter operably linked to a heterologous transcribable DNA molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing heterologous polynucleic acid molecules into plant cells. The method generally comprises the steps of selecting a suitable host cell, transforming the host cell with a recombinant vector, and obtaining the transformed host cell. Suitable methods include bacterial infection (e.g., *Agrobacterium*), binary bacterial artificial chromosome vectors, direct delivery of DNA (e.g., via PEG-mediated transformation, desiccation/inhibition-mediated DNA uptake, electroporation, agitation with silicon carbide fibers, and acceleration of DNA coated particles, etc. (reviewed in Potrykus et al., *Ann. Rev. Plant Physiol. Plant Mol. Biol.*, 42: 205 (1991)).

Technology for introduction of a heterologous DNA molecule into cells is well known to those of skill in the art. Methods and materials for transforming plant cells by introducing a plant DNA construct into a plant genome in the practice of this invention can include any of the well-known and demonstrated methods including, but not limited to:

(1) chemical methods (Graham and Van der Eb, *Virology*, 54(2):536-539 (1973) and Zatloukal et al., *Ann. N.Y. Acad. Sci.*, 660: 136-153 (1992));

(2) physical methods such as microinjection (Capecchi, *Cell*, 22(2):479-488 (1980)), electroporation (Wong and Neumann, *Biochim. Biophys. Res. Commun.*, 107(2): 584-587 (1982); Fromm, et al, *Proc. Natl. Acad. Sci. USA*, 82(17):5824-5828 (1985); U.S. Pat. No. 5,384,253, which is hereby incorporated by reference) particle acceleration (Johnston and Tang, *Methods Cell Biol.*, 43(A):353-365 (1994); Fynan et al., *Proc. Natl. Acad. Sci. USA*, 90(24):11478-11482 (1993)): and microprojectile bombardment (as illustrated in U.S. Pat. Nos. 5,015,580; 5,550,318; 5,538,880; 6,160,208; 6,399,861; and 6,403,865, all of which are hereby incorporated by reference);

(3) viral vectors (Clapp, *Clin. Perinatol.*, 20(1):155-168 (1993); Lu et al., *J. Exp. Med.*, 178(6):2089-2096 (1993); Eglitis and Anderson, *Biotechniques*, 6(7):608-614 (1988));

(4) receptor-mediated mechanisms (Curiel et al., *Hum. Gen. Ther.*, 3(2):147-154 (1992) and Wagner et al., *Proc. Natl. Acad. Sci. USA*, 89(13):6099-6103 (1992);

(5) bacterial mediated mechanisms such as *Agrobacterium*-mediated transformation (as illustrated in U.S. Pat. Nos. 5,824,877; 5,591,616; 5,981,840; and 6,384,301, all of which are hereby incorporated by reference);

(6) direct introduction into pollen by injecting a plant's reproductive organs (Zhou et al., *Methods in Enzymology*, 101:433, (1983); Hess, *Intern Rev. Cytol.*, 107:367 (1987); Luo et al., *Plant Mol Biol. Reporter*, 6:165 (1988); Pena et al., *Nature*, 325:274 (1987));

(7) protoplast transformation (as illustrated in U.S. Pat. No. 5,508,184, which is hereby incorporated by reference); and (8) injection into immature embryos (Neuhaus et al., *Theor. Appl. Genet.*, 75:30 (1987)).

Any of the above described methods may be utilized to transform a host cell with one or more chimeric promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; and 5,518,908); soybean (U.S. Pat. No. 5,569,834 and 5,416,011; see also, McCabe et al., *Biotechnolgy*, 6:923 (1988) and Christou et al., *Plant Physiol.* 87:671-674 (1988)); *Brassica* (U.S. Pat. No. 5,463,174); peanut (Cheng et al., *Plant Cell Rep.*, 15:653-657 (1996) and McKently et al., *Plant Cell Rep.*, 14:699-703 (1995)); papaya; and pea (Grant et al., *Plant Cell Rep.*, 15:254-258 (1995)).

Transformations of monocotyledon plants using electroporation, particle bombardment, and *Agrobacterium* have also been reported. Transformation and plant regeneration have been achieved in asparagus (Bytebier et al., *Proc. Natl. Acad. Sci. (USA)*, 84:5354 (1987); barley (Wan and Lemaux, *Plant Physiol*, 104:37 (1994)); maize (Rhodes et al., *Science* 240: 204 (1988), Gordon-Kamm et al., *Plant Cell*, 2:603-618 (1990), Fromm et al., *Bio/Technology*, 8:833 (1990), Koziel et al., *Bio/Technology*, 11:194 (1993), and Armstrong et al., *Crop Science*, 35:550-557 (1995)); oat (Somers et al., *Bio/Technology*, 10:1589 (1992)); orchard grass (Horn et al., *Plant Cell Rep.* 7:469 (1988)); rye (De la Pena et al., *Nature*, 325:274 (1987)); sugarcane (Bower and Birch, *Plant Journal*, 2:409 (1992)); tall fescue (Wang et al., *Bio/Technology*, 10:691 (1992)); and wheat (Vasil et al., *Bio/Technology*, 10:667 (1992) and U.S. Pat. No. 5,631,152).

The regeneration, development, and cultivation of plants from transformed plant protoplast or explants is well known in the art (see, for example, Weissbach and Weissbach, *Methods for Plant Molecular Biology*, (Eds.), Academic Press, Inc., San Diego, Calif. (1988) and Horsch et al., *Science*, 227:1229-1231 (1985)). Transformed cells are generally cultured in the presence of a selective media, which selects for the successfully transformed cells and induces the regeneration of plant shoots and roots into intact plants (Fraley et al., *Proc. Natl. Acad. Sci. U.S.A.*, 80: 4803 (1983)). Transformed plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses*, 2nd Edition, Monograph., 16:249 (1987); Fehr, *Principles of variety development, Theory and Technique*, (Vol 1) and *Crop Species Soybean* (Vol 2), Iowa State Univ., Macmillian Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleic acid molecule to its progeny. Progeny includes any regenerable plant part or seed comprising the transgene derived from an ancestor plant. The transgenic plant is preferably homozygous for the transformed polynucleic acid molecule and transmits that sequence to all of it's offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immuno-precipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense. Each patent and other reference cited herein is herein is hereby incorporated by reference in its entirety.

EXAMPLES

Regulatory and chimeric regulatory elements useful to drive expression of an operably linked transcribable polynucleotide in transgenic plants were constructed and operably linked to specific intron elements. The expression of these regulatory and the chimeric regulatory elements operably linked to the specific intron elements were used to drive transcription of a transcribable polynucleotide molecule encoding a polypeptide molecule, EPSPS (aroA:CP4), which confers resistance to the herbicide glyphosate in transgenic plants. Transgenic soy and tobacco plants transformed with plant binary plasmid constructs containing these chimeric regulatory elements and specific introns were analyzed to determine if expression driven by the chimeric regulatory molecule in combination with specific intron elements confers both vegetative and reproductive tolerance in plants sprayed with glyphosate.

Example 1

Construction of Regulatory and Chimeric Regulatory Elements and Plant Transformation Binary Plasmid Constructs This example describes the cloning of regulatory and chimeric regulatory elements which were operably linked to specific intron elements and are useful in driving transcription. Methods used to construct the chimeric regulatory elements are well known to those skilled in the art, such as restriction endonuclease cloning. Regulatory elements (promoters, enhancers, leaders and introns) were derived from the plant genes, AtTsf1 (*Arabidopsis thaliana* elongation factor 1α), Nte1F4A10 (*Nicotiana tabacum* initiation factor 4A10), AtAct7 (*Arabidopsis thaliana* actin 7), At.enr-A (*Arabidopsis thaliana* enoyl-ACP reductase) and At.EF1beta (*Arabidopsis thaliana* elongation factor-1 beta) and when operably linked to a herbicide tolerance protein encoding sequence will provide a level of herbicide tolerance to a transgenic plant expressing the protein. In order to create a chimeric regulatory element with enhanced expression, constitutive and pollen tissue expressing plant regulatory elements were combined with fragments comprising promoter, enhancer and leader elements to create new chimeric regulatory elements and operably linked to specific introns to confer vegetative and reproductive tolerance when operably linked to an herbicide tolerance protein encoding sequence.

The chimeric regulatory elements and their constituent parts are presented in Table 1 below. Regulatory and chimeric regulatory elements are presented as SEQ ID NOS: 1, 5, 9, 14, 16, 20, 24, 26, 28, 32, 35, 38 and 41. Promoter elements are presented as SEQ ID NOS: 2, 6, 12, 17, 21, 25, 27, 29, 33, 36, 39 and 42. Enhancer sequences are presented as SEQ ID NOS: 10, 11 and 15. Leader sequences are presented as SEQ ID NOS: 3, 7, 18, 22, 30, 37 and 40. Intron sequences are presented as SEQ ID NOS: 4, 8, 13, 19, 23, 31 and 34.

TABLE 1

Regulatory Elements and Constituent Enhancers, Promoters and Leaders

| SEQ ID NO: | Annotation |
|---|---|
| 1 | EXP-At.Tsf1 |
| 2 | P-At.Tsf1-1:1:6 |
| 3 | L-At.Tsf1-1:1:1 |
| 4 | I-At.Tsf1-1:1:8 |
| 5 | EXP-At.Act7 |
| 6 | P-At.Act7-1:1:3 |
| 7 | L-At.Act7-1:1:2 |
| 8 | I-At.Act7-1:1:2 |
| 9 | EXP-At.Act7/At.Tsf1/At.Tsf1 |
| 10 | E-At.Act7-1:1:1 |
| 11 | E-At.Tsf1-1:1:1 |
| 12 | P-At.Tsf1-1:1:11 |
| 13 | I-At.Tsf1-1:1:11 |
| 14 | EXP-At.Tsf1/At.Act7/At.Tsf1 |
| 15 | E-At.Act7-1:1:2 |
| 16 | EXP-At.EF1beta |
| 17 | P-At.EF1beta-0:0:1 |
| 18 | L-At.EF1beta-0:0:2 |
| 19 | I-At.EF1beta-0:0:1 |
| 20 | EXP-At.Tsf1/Nt.eIF-4A10 |
| 21 | P-Nt.eIF-4A10-0:0:2 |
| 22 | L-Nt.eIF4A10-1:1:1 |
| 23 | I-Nt.eIF4A10-0:0:2 |
| 24 | EXP-At.Tsf1/At.EF1beta |
| 25 | P-At.EF1beta-0:0:2 |
| 26 | EXP-At.Tsf1/At.Act7 |
| 27 | P-At.Act7-1:1:5 |
| 28 | EXP-At.Tsf1/At.enr-A |
| 29 | P-At.enr-A-0:0:4 |
| 30 | L-At.enr-A-0:0:2 |
| 31 | I-At.enr-A-0:0:1 |
| 32 | EXP-Nt.eIF4A10 |
| 33 | P-Nt.eIF4A10-1:1:1 |
| 34 | I-Nt.eIF4A10-1:1:1 |
| 35 | EXP-At.Act7/Nt.eIF4A10 |
| 36 | P-Nt.eIF4A10-1:1:5 |
| 37 | L-Nt.eIF4A10-1:1:2 |
| 38 | EXP-FMV/Ph.DnaK |
| 39 | P-FMV.35S-1:1:3 |
| 40 | L-Ph.DnaK-1:1:2 |
| 41 | EXP-At.Act7/At.Tsf1 |
| 42 | P-At.Tsf1-1:1:7 |

The regulatory element, EXP-At.Tsf1 (SEQ ID NO: 1) is comprised of a promoter, P-At.Tsf1-1:1:6 (SEQ ID NO: 2) operably linked 5' to a leader, L-At.Tsf1-1:1:1 (SEQ ID NO: 3). The regulatory element, EXP-At.Act7 (SEQ ID NO: 5) is comprised of a promoter, P-At.Act7-1:1:3 (SEQ ID NO: 6) operably linked 5' to a leader, L-At.Act7-1:1:2 (SEQ ID NO: 7). The chimeric regulatory element, EXP-At.Act7/At.Tsf1/Tsf1 (SEQ ID NO: 9) is comprised of an enhancer, E-At.Act7-1:1:1 (SEQ ID NO: 10) operably linked 5' to an enhancer, E-At.Tsf1-1:1:1 (SEQ ID NO: 11), operably linked 5' to a promoter, P-At.Tsf1-1:1:11 (SEQ ID NO: 12), operably linked 5' to a leader, L-At.Tsf1-1:1:1 (SEQ ID NO: 3). The chimeric regulatory element, EXP-At.Tsf1/At.Act7/At.Tsf1 (SEQ ID NO: 14) is comprised of an enhancer, E-At.Tsf1-1:1:1 (SEQ ID NO: 11), operably linked 5' to an enhancer, E-At.Act7-1:1:2 (SEQ ID NO:15), operably linked 5' to a promoter, P-AtTsf1-1:1:11 (SEQ ID NO: 12), operably linked 5' to a leader, L-At.Tsf1-1:1:1 (SEQ ID NO: 3). The regulatory element, EXP-At.EF1beta (SEQ ID NO: 16) is comprised of a promoter, P-At.EF1beta-0:0:1 (SEQ ID NO: 17), operably linked 5' to a leader, L-At.EF1beta-0:0:2 (SEQ ID NO: 18). The chimeric regulatory element, EXP-At.Tsf1/Nt.e1F-4A10 (SEQ ID NO: 20) is comprised of an enhancer, E-At.Tsf1-1:1:1 (SEQ ID NO: 11), operably linked 5' to a promoter, P-Nt.eIF-4A10-0:0:2 (SEQ ID NO: 21), operably linked 5' to a leader, L-Nt.eIF4A10-1:1:1 (SEQ ID NO: 22). The chimeric regulatory element, EXP-At.Tsf1/At.EF1beta (SEQ ID NO: 24) is comprised of an enhancer, E-At.Tsf1-1:1:1 (SEQ ID NO: 11), operably linked 5' to a promoter, P-At.EF1beta-0:0:2 (SEQ ID NO: 25), operably linked 5' to a leader, L-At.EF1beta-0:0:2 (SEQ ID NO: 18). The chimeric regulatory element, EXP-At.Tsf1/At.Act7 (SEQ ID NO: 26) is comprised of an enhancer, E-At.Tsf1-1:1:1 (SEQ ID NO: 11), operably linked 5' to a promoter, P-At.Act7-1:1:5 (SEQ ID NO: 27), operably linked 5' to a leader, L-At.Act7-1:1:2 (SEQ ID NO: 7). The chimeric regulatory element, EXP-At.Tsf1At.enr-A (SEQ ID NO: 28) is comprised of an enhancer, E-At.Tsf1-1:1:1 (SEQ ID NO: 11), operably linked 5' to a promoter, P-At.enr-A-0:0:4 (SEQ ID NO: 29), operably linked 5' to a leader, L-At.enr-A-0:0:2 (SEQ ID NO: 30). The regulatory element, EXP-Nt.e1F4A10 (SEQ ID NO: 32) is comprised of a promoter, P-Nt.eIF4A10-1:1:1 (SEQ ID NO: 33), operably linked 5' to a leader, L-Nt.eIF4A10-1:1:1 (SEQ ID NO: 22). The chimeric regulatory, EXP-At.Act7/Nt.e1F4A10 (SEQ ID NO: 35) is comprised of an enhancer, E-At.Act7-1:1:1 (SEQ ID NO: 10), operably linked 5' to a promoter, P-Nt.eIF4A10-1:1:5 (SEQ ID NO: 36), operably linked 5' to a leader, L-Nt.eIF4A10-1:1:2 (SEQ ID NO: 37). The chimeric regulatory element, EXP-FMV/Ph.DnaK (SEQ ID NO: 38) is comprised of a promoter, P-FMV.35S-1:1:3 (SEQ ID NO: 39), operably linked 5' to a leader, L-Ph.DnaK-1:1:2 (SEQ ID NO: 40). The chimeric regulatory element, EXP-At.Act7/At.Tsf1 (SEQ ID NO: 41) is comprised of an enhancer, E-At.Act7-1:1:1 (SEQ ID NO: 10), operably linked 5' to a promoter, P-At.Tsf1-1:1:7 (SEQ ID NO: 42), operably linked 5' to a leader, L-ALTsf1-1:1:1 (SEQ ID NO: 3).

The regulatory and chimeric regulatory elements were cloned using methods known in the art into plant transformation binary plasmid constructs and were operably linked 5' to an intron element which in turn was operably linked 5' to plastid targeted EPSPS coding sequence which was operably linked 5' to a 3' UTR (T-Ps.RbcS2-E9-1:1:3, SEQ ID NO: 43 or T-AGRtu.nos-1:1:13, SEQ ID NO: 44). Table 2 shows the plasmid constructs and their corresponding regulatory or chimeric regulatory elements, introns and 3' UTR.

TABLE 2

Plant Transformation Constructs and Corresponding Regulatory or Chimeric Regulatory Elements, Introns and 3' UTRs.

| Binary Plasmid Construct | Regulatory or Chimeric Regulatory Element | Regulatory or Chimeric Regulatory Element SEQ ID NO: | Intron | Intron SEQ ID NO: | 3' UTR |
|---|---|---|---|---|---|
| pMON45331 | EXP-At.Tsf1 | 1 | I-At.Tsf1-1:1:8 | 4 | T-Ps.RbcS2-E9-1:1:3 |
| pMON54955 | EXP-At.Act7 | 5 | I-At.Act7-1:1:2 | 8 | T-AGRtu.nos-1:1:13 |
| pMON65391 | EXP-At.Act7/At.Tsf1/At.Tsf1 | 9 | I-At.Tsf1-1:1:11 | 13 | T-Ps.RbcS2-E9-1:1:3 |
| pMON65392 | EXP-At.Tsf1/At.Act7/At.Tsf1 | 14 | I-At.Tsf1-1:1:11 | 13 | T-Ps.RbcS2-E9-1:1:3 |
| pMON71532 | EXP-At.EF1beta | 16 | I-At.EF1beta-0:0:1 | 19 | T-Ps.RbcS2-E9-1:1:3 |
| pMON71537 | EXP-At.Tsf1/Nt.eIF-4A10 | 20 | I-Nt.eIF4A10-0:0:2 | 23 | T-Ps.RbcS2-E9-1:1:3 |
| pMON71538 | EXP-At.Tsf1/At.EF1beta | 24 | I-At.EF1beta-0:0:1 | 19 | T-Ps.RbcS2-E9-1:1:3 |
| pMON71541 | EXP-At.Tsf1/At.Act7 | 26 | I-At.Act7-1:1:2 | 8 | T-Ps.RbcS2-E9-1:1:3 |
| pMON71543 | EXP-At.Tsf1/At.enr-A | 28 | I-At.enr-A-0:0:1 | 31 | T-Ps.RbcS2-E9-1:1:3 |
| pMON73663 | EXP-Nt.eIF4A10 | 32 | I-Nt.eIF4A10-1:1:1 | 34 | T-Ps.RbcS2-E9-1:1:3 |
| pMON73671 | EXP-At.Act7/Nt.eIF4A10 | 35 | I-Nt.eIF4A10-1:1:1 | 34 | T-Ps.RbcS2-E9-1:1:3 |
| pMON81508 | EXP-FMV/Ph.DnaK | 38 | No Intron | | T-Ps.RbcS2-E9-1:1:3 |
| pMON81703 | EXP-At.Act7/At.Tsf1 | 41 | I-At.Tsf1-1:1:11 | 13 | T-Ps.RbcS2-E9-1:1:3 |

The resulting expression cassette was comprised 5' to 3' of a T-DNA right border sequence, a regulatory or chimeric regulatory element, operably linked 5' to an intron element (except for pMON81508), operably linked 5' to a short DNA fragment to permit proper intron/exon splicing, operably linked 5' to a plastid targeted EPSPS coding sequence (aroA: CP4), operably linked 5' to a 3' UTR followed by a T-DNA left border sequence.

Example 2

Evaluation of Regulatory and Chimeric Regulatory Elements and Introns in Transgenic Soybean Plants The plant transformation plasmid constructs described in example 1 above were used to transform soybean plants using *Agrobacterium tumefaciens*-mediated transformation methods known in the art. The resulting transgenic soybean plants were tested at R1 generation for vegetative tolerance to glyphosate and at R2 generation for reproductive tolerance to glyphosate.

The DNA constructs, pMON45331, pMON54955, pMON65391, pMON65392, pMON71532, pMON71537, pMON71538, pMON71541, pMON71543, pMON73663 and pMON73671 were used to transform soybean (*Glycine max*) by an *Agrobacterium* mediated method (for example, see U.S. Pat. Nos. 6,384,301, 5,569,834, and 5,416,011, herein incorporated by reference). R1 and R2 transgenic soybean plants were tested for vegetative and reproductive tolerance, respectively as described in U.S. Patent Application 2006/0236420 (herein incorporated by reference).

$R_1$ soybean plants were tested for vegetative tolerance to glyphosate. For the $R_1$ evaluations, typically 48 seeds per event were planted and an ELISA analysis was performed to identify the positive transformants and to determine the segregation ratio. Plants were typically sprayed with approximately 52 ounces/acre of Roundup UltraMax II® (Registered trademark of Monsanto Technology LLC, St. Louis Mo.) herbicide at the V1 stage. Approximately one week post-spray the events were evaluated for chlorosis. Copy number and zygosity were also assessed using quantitative PCR. The quantitative PCR reaction was performed in a Real Time PCR system manufactured by Applied Biosystems (Foster City, Calif.). All reagents, including custom primers and probes were purchased from Applied Biosystems and were used according to the instructions provided by the manufacturer. Other observations taken included: emergence, segregation, pod set (timing of), plant height, and maturity. Those events that had one copy of the transgene, no vector backbone, and vegetative glyphosate tolerance were advanced to the $R_2$ nursery to evaluate reproductive tolerance, these events are referred to as the $R_2$ events. Plants from the $R_2$ events were tested for reproductive tolerance to glyphosate. Plants treated with Roundup UltraMax II® that were morphologically similar to non-treated plants and which also produced seeds were considered tolerant. Data showing enhanced reproductive tolerance are provided in Table 3.

TABLE 3

Vegetative and Reproductive Tolerance of Transgenic Soybean Plants

| Binary Plasmid Construct | Regulatory or Chimeric Regulatory Element | Intron | % $R_1$ Vegetative Tolerance | % $R_2$ Reproductive Tolerance |
|---|---|---|---|---|
| pMON45331 | EXP-At.Tsf1 | I-At.Tsf1-1:1:8 | 13 | 3 |
| pMON54955 | EXP-At.Act7 | I-At.Act7-1:1:2 | 25 | 25 |
| pMON65391 | EXP-At.Act7/At.Tsf1/At.Tsf1 | I-At.Tsf1-1:1:11 | 20 | 0 |
| pMON65392 | EXP-At.Tsf1/At.Act7/At.Tsf1 | I-At.Tsf1-1:1:11 | 80 | 20 |
| pMON71532 | EXP-At.EF1beta | I-At.EF1beta-0:0:1 | 0 | 0 |
| pMON71537 | EXP-At.Tsf1/Nt.eIF-4A10 | I-Nt.eIF4A10-0:0:2 | 0 | 0 |
| pMON71538 | EXP-At.Tsf1/At.EF1beta | I-At.EF1beta-0:0:1 | 0 | 0 |
| pMON71541 | EXP-At.Tsf1/At.Act7 | I-At.Act7-1:1:2 | 50 | 14 |
| pMON71543 | EXP-At.Tsf1/At.enr-A | I-At.enr-A-0:0:1 | 0 | 0 |
| pMON73663 | EXP-Nt.eIF4A10 | I-Nt.eIF4A10-1:1:1 | 40 | 13 |
| pMON73671 | EXP-At.Act7/Nt.eIF4A10 | I-Nt.eIF4A10-1:1:1 | 68 | 50 |

Several constructs, when used to transform soybean, conferred both vegetative and reproductive tolerance. The three constructs that provided the best reproductive tolerance were pMON54955, which contains the regulatory element EXP-At.Act7 (SEQ ID NO: 5) combined with the intron, I-At.Act7-1:1:2 (SEQ ID NO: 8), pMON65392, which contains the chimeric regulatory element, EXP-At.Tsf1/At.Act7/At.Tsf1 (SEQ ID NO: 9) combined with the intron, I-At.Tsf1-1:1:11 (SEQ ID NO: 13) and pMON73671, which contains the chimeric regulatory element, EXP-At.Act7/Nt.eIF4A10 (SEQ ID NO: 35) and the intron, I-Nt.eIF4A10-1:1:1 (SEQ ID NO: 34). Three other constructs provided reproductive tolerance in a lower percentage of events. These three constructs were, pMON45331, which contained the regulatory element, EXP-At.Tsf1 (SEQ ID NO: 1) combined with the intron, I-ALTsf1-1:1:8 (SEQ ID NO: 4), pMON71541, which contained the chimeric regulatory element, EXP-At.Tsf1/At.Act7 (SEQ ID NO: 26) combined with the intron, I-At.Act7-1:1:2 (SEQ ID NO: 8) and pMON73663, which contains the regulatory element, EXP-Nt.eIF4A10 (SEQ ID NO: 32) combined with the intron, I-Nt.eIF4A10-1:1:1 (SEQ ID NO: 34). All 6 of the above described constructs provided a level of reproductive tolerance and would be useful in producing transgenic soybean plants with vegetative and reproductive herbicide tolerance. Constructs containing the specific regulatory element combinations contained within the above constructs, when operably linked to an herbicide tolerance conferring coding sequence, would be expected to provide a level of vegetative and reproductive tolerance to selected events. One construct, pMON65391, provided vegetative but not reproductive tolerance. This construct contained the chimeric regulatory element, EXP-At.Act7/At.Tsf1/At.Tsf1 (SEQ ID NO: 9) combined with the intron, I-At.Tsf1-1:1:11 (SEQ ID NO: 13). Constructs containing the specific regulatory element combination contained within pMON65391, when operably linked to an herbicide tolerance conferring coding sequence, would be expected to provide a level of vegetative tolerance to selected events. This would be useful in such applications such as providing a transformed plant that can be used in hybrid seed production.

Example 3

Evaluation of Regulatory and Chimeric Regulatory Elements and Introns in Transgenic Tobacco Plants Selected plant transformation plasmid constructs described in example 1 above (pMON81703, pMON73663 and pMON81508) were used to transform tobacco plants using *Agrobacterium tumefaciens*-mediated transformation methods known in the art. *Nicotiana tabacum* cv. *Nicotiana samsun* was transformed by using the leaf disc method (Horsch et al. (1985) *Science* 227:1229-1231 and Horsch et al. (1987) *Plant Tissue and Cell Culture* pp. 317-329, Alan R. Liss, Inc.). Tobacco shoots were rooted in MS media (R0 plants) and then transferred to soil. Tobacco plants were analyzed for glyphosate tolerance at the R0 stage. After 38 days of growth in soil 30 to 35 plants per construct were sprayed with 96 ounces/acre Roundup® Ultra (Monsanto Technology LLC, St. Louis Mo.) herbicide. Control plants were sprayed with 0 ounces/acre. Plants were scored for vegetative tolerance to glyphosate and for fertility. Plants with vegetative damage were discarded. Plants treated with glyphosate that were morphologically similar to non-treated plants and also produced viable seeds were considered to demonstrate reproductive tolerance.

The result of the analysis for the constructs tested in transgenic tobacco plants is provided in Table 4. Glyphosate tolerance was scored for both vegetative and reproductive tissues as the percentage of the EPSPS-expressing plants tested that were glyphosate tolerant.

TABLE 4

Vegetative and Reproductive Glyphosate Tolerance in Transgenic Tobacco Plants

| Binary Plasmid Construct | Regulatory or Chimeric Regulatory Element | Intron | % R0 Vegetative Tolerance | % R0 Reproductive Tolerance |
|---|---|---|---|---|
| pMON81703 | EXP-At.Act7/At.Tsf1 | I-At.Tsf1-1:1:11 | 66 | 22 |
| pMON73663 | EXP-Nt.eIF4A10 | I-Nt.eIF4A10-1:1:1 | 71 | 6 |
| pMON81508 | EXP-FMV/Ph.DnaK | No Intron | 60 | 0 |

Both pMON81703, which contained the chimeric regulatory element, EXP-At.Act7/At.Tsf1 (SEQ ID NO: 41) combined with the intron, I-ALTsf1-1:1:11 (SEQ ID NO: 13) and pMON73663, which contained the regulatory element, EXP-Nt.eIF4A10 (SEQ ID NO: 30) combined with the intron, I-Nt.eIF4A10-1:1:1 (SEQ ID NO: 34) provided events with both vegetative and reproductive tolerance. Constructs containing the specific regulatory element combinations contained within the above constructs, when operably linked to an herbicide tolerance conferring coding sequence, would be expected to provide a level of vegetative and reproductive tolerance to selected events.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are hereby incorporated by reference to the same extent as if each individual publication or patent application is specifically and individually indicated to be incorporated by reference.

I claim:

1. A DNA molecule comprising a chimeric promoter sequence comprising, as operably linked components:
   a) a first DNA sequence comprising:
      i) SEQ ID NO:33; or
      ii) a DNA sequence with at least 95 percent sequence identity to SEQ ID NO:33 having promoter activity; or
      ii) a fragment comprising at least 50 contiguous nucleotides of SEQ ID NO:33 having promoter activity; and
   b) a heterologous DNA sequence comprising:
      i) SEQ ID NO:10; or
      ii) a DNA sequence with at least 95 percent sequence identity to SEQ ID NO:10 having enhancer activity; or
      ii) a fragment comprising at least 50 contiguous nucleotides of SEQ ID NO:33 having enhancer activity.

2. The DNA molecule of claim 1, wherein the chimeric promoter sequence comprises, as operably linked components: a) a fragment comprising at least 50 contiguous nucleotides of SEQ ID NO: 33 having promoter activity; and b) a fragment comprising at least 50 contiguous nucleotides of SEQ ID NO: 10 having enhancer activity.

3. The DNA molecule of claim 1, wherein the heterologous sequence is SEQ ID NO: 5, or a fragment thereof comprising at least 50 contiguous nucleotides of SEQ ID NO: 5 and having enhancer activity.

4. The DNA molecule of claim 1, wherein the chimeric promoter sequence is SEQ ID NO: 46; or a DNA sequence with at least 95 percent sequence identity to SEQ ID NO: 46.

5. The DNA molecule of claim 1, wherein said chimeric promoter is operably linked to a transcribable DNA molecule.

6. The DNA molecule of claim 5, wherein the transcribable DNA molecule is a gene of agronomic interest.

7. The DNA molecule of claim 6, wherein the transcribable DNA molecule is a gene capable of providing herbicide resistance in plants.

8. The DNA molecule of claim 6, wherein the transcribable DNA molecule is a gene capable of providing plant pest control in plants.

9. A transgenic plant cell stably transformed with the DNA molecule of claim 1, wherein said DNA molecule is operably linked to a transcribable DNA molecule.

10. The transgenic plant cell of claim 9, wherein said transgenic plant cell is a dicotyledonous plant cell.

11. The transgenic plant cell of claim 10, wherein said transgenic plant cell is selected from the group consisting of a tobacco plant cell, tomato plant cell, potato plant cell, soybean plant cell, cotton plant cell, canola plant cell, sunflower plant cell and alfalfa plant cell.

12. A transgenic plant or plant part comprising the DNA molecule of claim 1.

13. A seed produced from the transgenic plant of claim 12, wherein the seed comprises said DNA molecule.

14. A progeny plant of the transgenic plant of claim 12 or a part thereof, wherein the progeny plant comprises said DNA molecule.

15. A method of producing a progeny plant comprising: a) growing said transgenic plant of claim 12 to a reproductive stage, and; b) crossing said transgenic plant with another plant to produce said progeny plant.

16. A method of providing a plant with a beneficial agronomic trait comprising expressing in the plant a DNA molecule of claims 1, wherein the DNA molecule is operably linked to a transcribable DNA molecule capable of providing said beneficial agronomic trait.

17. The method of claim 16, wherein said plant with said beneficial agronomic trait is selected from the group consisting of wheat, maize, rye, rice, corn, oat, barley, sorghum, millet, tobacco, tomato, potato, soybean, cotton, canola, sunflower and alfalfa, asparagus, avocado, banana, barley, beans, beet, blackberry, blueberry, broccoli, brussel sprouts, cabbage, canola, cantaloupe, carrot, cassava, cauliflower, celery, cherry, cilantro, cucumber, eggplant, honey dew, jicama, lettuce, leeks, melon, onion, papaya, parsley, pea, peanut, pepper, plum, pomegranate, poplar, potato, pumpkin, quince, radish, raspberry, spinach, squash, strawberry, sugarbeet, sugarcane, sweet potato, tobacco, tomato, watermelon, yams, and zucchini.

18. The method of claim 16, wherein said transcribable DNA molecule capable of providing said beneficial agronomic trait is a gene controlling the phenotype of a trait selected from the group consisting of: herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

* * * * *

UNITED STATES PATENT AND TRADEMARK OFFICE
CERTIFICATE OF CORRECTION

PATENT NO.        : 8,846,892 B2                                   Page 1 of 1
APPLICATION NO.   : 13/062945
DATED             : September 30, 2014
INVENTOR(S)       : Stanislaw Flasinski It is certified that error appears in the above-identified patent and that said Letters Patent is hereby corrected as shown below:

In the Claims

Column 69, Line 29, please delete "ii)" and insert --iii)--

Column 69, Line 37, please delete "ii)" and insert --iii)--

Column 69, Line 38, please delete "SEQ ID NO:33" and insert --SEQ ID NO:10--

Signed and Sealed this
Third Day of February, 2015

Michelle K. Lee
*Deputy Director of the United States Patent and Trademark Office*

SEQUENCE LISTING

<160> NUMBER OF SEQ ID NOS: 52

<210> SEQ ID NO 1
<211> LENGTH: 1773
<212> TYPE: DNA
<213> ORGANISM: Arabidopsis thaliana

<400> SEQUENCE: 1

```
cgtatgccaa aacttgttca tcgtgttata tattaaacaa caccttctgt tctgacgata        60
aaaaatgaaa ggcaatagta ataatttagc aaaaactaac aagacatcgg atttatttat       120
cctgtgacta gatgtacttg gatcatgtaa ctggagaaat cctacacatg agtgtgctca       180
caggcgtttt tatttcttgt tctggctgtt ctctacttca ttcttttagc tctagctcct       240
```

```
gttggttgct tctgacctgt tttccttctg attttcttg ttgtagactc gagtcaacaa    300
aaggaacata tgcagcggaa tggaccaaat gggagaaaca actacgagat actctagttg    360
caaattctga gtatctcagt tctattcagg taaaaaattc ctttgtcatt gatggctcat    420
gaaaagcaag aaatctgcga ttgaatttta aactgcttca atgttccttc agtacatggt    480
aaaagagtat aagaagaagg atgtacatat gatgtctttg ttttctggtt tgcaactttc    540
aggttccatt tgagtctatg gttcatcaag tgcgagaaga gctaaaaaca atagcgaagg    600
gtgattacaa gccaccaagt tcggagaaaa gaaaacacgg gtctattgtt ttcgctgcca    660
tcaacttgcc tgctactcaa gttcacagtc ttcttgaaaa ggtaaccaac caatttctta    720
tactatcata taaaaaaaca aaggaatat tgagacaaga actcttcaac tgccgaaaac    780
taaaggttaa gtatgggctt tgttattaat taatagatgt tattcttatc agttggctgc    840
agcaaaccca acaatgagat cttttctaga gggaagaaa aagagcatac aggaaaaact    900
tgaacggtct cacgtgacgc tcgcccacaa gagaagccat ggcgtagcaa ctgtagccag    960
ctatagtcag cacttgaaca gagaggtacc cgtagagctc accgagctca tctacaacga   1020
caagatggct gctctaacag cccatgttgg atctgtggac ggagagaccg tagtctccaa   1080
gaacgaatgg ccacatgtta cattgtggac agcggaaggc gttactgcga aagaggccaa   1140
cacgttacct cagctttact agaaggaaa ggcgagccgc ttggtgatag atcctccggt   1200
gtcaatctca ggtcctctgg agttttttctg aatacttgat taaacatgga agtttctctc   1260
ttgagggagg ttgctcgtgg aatgggacac atatggttgt tataataaac catttccatt   1320
gtcatgagat tttgaggtta atatatactt tacttgttca ttatttttatt tggtgtttga   1380
ataaatgata taaatggctc ttgataatct gcattcattg agatatcaaa tatttactct   1440
agagaagagt gtcatataga ttgatggtcc acaatcaatg aaattttgg gagacgaaca   1500
tgtataacca tttgcttgaa taaccttaat taaaaggtgt gattaaatga tgtttgtaac   1560
atgtagtact aaacattcat aaaacacaac caacccaaga ggtattgagt attcacggct   1620
aaacaggggc ataatggtaa tttaaagaat gatattattt tatgttaaac cctaacattg   1680
gtttcggatt caacgctata aataaaacca ctctcgttgc tgattccatt tatcgttctt   1740
attgacccta gccgctacac acttttctgc gat                                 1773
```

<210> SEQ ID NO 2
<211> LENGTH: 1727
<212> TYPE: DNA
<213> ORGANISM: Arabidopsis thaliana

<400> SEQUENCE: 2

```
cgtatgccaa aacttgttca tcgtgttata tattaaacaa caccttctgt tctgacgata     60
aaaaatgaaa ggcaatagta ataatttagc aaaaactaac aagacatcgg atttatttat    120
cctgtgacta gatgtacttg gatcatgtaa ctggagaaat cctacacatg agtgtgctca    180
caggcgtttt tatttcttgt tctggctgtt ctctacttca ttcttttagc tctagctcct    240
gttggttgct tctgacctgt tttccttctg attttcttg ttgtagactc gagtcaacaa    300
aaggaacata tgcagcggaa tggaccaaat gggagaaaca actacgagat actctagttg    360
caaattctga gtatctcagt tctattcagg taaaaaattc ctttgtcatt gatggctcat    420
gaaaagcaag aaatctgcga ttgaatttta aactgcttca atgttccttc agtacatggt    480
aaaagagtat aagaagaagg atgtacatat gatgtctttg ttttctggtt tgcaactttc    540
aggttccatt tgagtctatg gttcatcaag tgcgagaaga gctaaaaaca atagcgaagg    600
```

```
gtgattacaa gccaccaagt tcggagaaaa gaaaacacgg gtctattgtt ttcgctgcca      660
tcaacttgcc tgctactcaa gttcacagtc ttcttgaaaa ggtaaccaac caatttctta      720
tactatcata taaaaaaaca aaaggaatat tgagacaaga actcttcaac tgccgaaaac      780
taaaggttaa gtatgggctt tgttattaat taatagatgt tattcttatc agttggctgc      840
agcaaaccca acaatgagat cttttctaga gggaagaaa aagagcatac aggaaaaact      900
tgaacggtct cacgtgacgc tcgcccacaa gagaagccat ggcgtagcaa ctgtagccag      960
ctatagtcag cacttgaaca gagaggtacc cgtagagctc accgagctca tctacaacga     1020
caagatggct gctctaacag cccatgttgg atctgtggac ggagagaccg tagtctccaa     1080
gaacgaatgg ccacatgtta cattgtggac agcggaaggc gttactgcga agaggccaa      1140 cacgttacct cagctttact agaaggaaa ggcgagccgc ttggtgatag atcctccggt     1200
gtcaatctca ggtcctctgg agttttctg aatacttgat taaacatgga agtttctctc     1260
ttgagggagg ttgctcgtgg aatgggacac atatggttgt tataataaac catttccatt     1320
gtcatgagat tttgaggtta atatatactt tacttgttca ttattttatt tggtgtttga     1380
ataaatgata taaatggctc ttgataatct gcattcattg agatatcaaa tatttactct     1440
agagaagagt gtcatataga ttgatggtcc acaatcaatg aaatttttgg gagacgaaca     1500
tgtataacca tttgcttgaa taaccttaat taaaaggtgt gattaaatga tgtttgtaac     1560
atgtagtact aaacattcat aaaacacaac caacccaaga ggtattgagt attcacggct     1620
aaacaggggc ataatggtaa tttaaagaat gatattattt tatgttaaac cctaacattg     1680
gtttcggatt caacgctata aataaaacca ctctcgttgc tgattcc                   1727

<210> SEQ ID NO 3
<211> LENGTH: 46
<212> TYPE: DNA
<213> ORGANISM: Arabidopsis thaliana

<400> SEQUENCE: 3
atttatcgtt cttattgacc ctagccgcta cacactttc tgcgat                      46

<210> SEQ ID NO 4
<211> LENGTH: 600
<212> TYPE: DNA
<213> ORGANISM: Arabidopsis thaliana

<400> SEQUENCE: 4
gtaagcgtta acgtacccct tagatcgttct ttttcttttt cgtctgctga tcgttgctca     60
tattatttcg atgattgttg gattcgatgc tctttgttga ttgatcgttc tgaaaattct      120
gatctgttgt ttagatttta tcgattgtta atatcaacgt ttcactactt ctaaacgata     180
atttattcat gaaactattt tcccattctg atcgatcttg ttttgagatt ttaatttgtt     240
cgattgattt ttggttggtg gatctatata cgagtgaact tgttgatttg cgtatttaag     300
atgtatgtcg atttgaattg tgattgggta attctggagt agcataacaa atccagtgtt     360
ccctttttct aagggtaatt ctcggattgt ttgctttata tctcttgaaa ttgccgattt     420
gattgaattt agctcgctta gctcagatga tagagcacca caattttgt ggtagaaatc      480 ggtttgactc cgatagcggc ttttactat gattgttttg tgttaaagat gattttcata      540
atggttatat atgtctactg ttttattga ttcaatattt gattgttctt ttttttgcag      600

<210> SEQ ID NO 5
```

<211> LENGTH: 694
<212> TYPE: DNA
<213> ORGANISM: Arabidopsis thaliana

<400> SEQUENCE: 5

```
actagtcaac aattggccaa tctttgttct aaattgctaa taaacgacca tttccgtcaa        60
ttctccttgg ttgcaacagt ctacccgtca atgtttact aatttataag tgtgaagttt       120
gaattatgaa agacgaaatc gtattaaaaa ttcacaagaa taaacaactc catagatttt       180
caaaaaaaca gtcacgagaa aaaaccaca gtccgtttgt ctgctcttct agttttatt        240
attttctat taatagtttt tgttatttc gagaataaaa tttgaacgat gtccgaacca        300
caaaagccga gccgataaat cctaagccga gcctaacttt agccgtaacc atcagtcacg       360
gctcccgggc taattcattt gaaccgaatc ataatcaacg gtttagatca aactcaaaac       420
aatctaacgg caacatagac gcgtcggtga gctaaaaaga gtgtgaaagc caggtcacca       480
tagcattgtc tctcccagat ttttatttg ggaaataata aagaaatag aaaaaaataa        540
aagagtgaga aaaatcgtag agctatatat tcgcacatgt actcgtttcg ctttccttag       600
tgttagctgc tgccgctgtt gtttctcctc catttctcta tctttctctc tcgctgcttc       660
tcgaatcttc tgtatcatct tcttcttctt caag                                  694
```

<210> SEQ ID NO 6
<211> LENGTH: 600
<212> TYPE: DNA
<213> ORGANISM: Arabidopsis thaliana

<400> SEQUENCE: 6

```
actagtcaac aattggccaa tctttgttct aaattgctaa taaacgacca tttccgtcaa        60
ttctccttgg ttgcaacagt ctacccgtca atgtttact aatttataag tgtgaagttt       120
gaattatgaa agacgaaatc gtattaaaaa ttcacaagaa taaacaactc catagatttt       180
caaaaaaaca gtcacgagaa aaaaccaca gtccgtttgt ctgctcttct agttttatt        240
attttctat taatagtttt tgttatttc gagaataaaa tttgaacgat gtccgaacca        300
caaaagccga gccgataaat cctaagccga gcctaacttt agccgtaacc atcagtcacg       360
gctcccgggc taattcattt gaaccgaatc ataatcaacg gtttagatca aactcaaaac       420
aatctaacgg caacatagac gcgtcggtga gctaaaaaga gtgtgaaagc caggtcacca       480
tagcattgtc tctcccagat ttttatttg ggaaataata aagaaatag aaaaaaataa        540
aagagtgaga aaaatcgtag agctatatat tcgcacatgt actcgtttcg ctttccttag       600
```

<210> SEQ ID NO 7
<211> LENGTH: 94
<212> TYPE: DNA
<213> ORGANISM: Arabidopsis thaliana

<400> SEQUENCE: 7

```
tgttagctgc tgccgctgtt gtttctcctc catttctcta tctttctctc tcgctgcttc        60
tcgaatcttc tgtatcatct tcttcttctt caag                                   94
```

<210> SEQ ID NO 8
<211> LENGTH: 544
<212> TYPE: DNA
<213> ORGANISM: Arabidopsis thaliana

<400> SEQUENCE: 8

```
gtgagtctct agatccgttc gcttgatttt gctgctcgtt agtcgttatt gttgattctc        60
```

```
tatgccgatt tcgctagatc tgtttagcat gcgttgtggt tttatgagaa aatctttgtt    120 ttggggttg cttgttatgt gattcgatcc gtgcttgttg gatcgatctg agctaattct     180
taaggtttat gtgttagatc tatggagttt gaggattctt ctcgcttctg tcgatctctc    240
gctgttattt ttgttttttt cagtgaagtg aagttgttta gttcgaaatg acttcgtgta    300
tgctcgattg atctggtttt aatcttcgat ctgttaggtg ttgatgttta caagtgaatt    360
ctagtgtttt ctcgttgaga tctgtgaagt ttgaacctag ttttctcaat aatcaacata    420
tgaagcgatg tttgagtttc aataaacgct gctaatcttc gaaactaagt tgtgatctga    480
ttcgtgttta cttcatgagc ttatccaatt catttcggtt tcattttact ttttttttag    540
tgaa                                                                  544

<210> SEQ ID NO 9
<211> LENGTH: 1085
<212> TYPE: DNA
<213> ORGANISM: Artificial sequence
<220> FEATURE:
<221> NAME/KEY: misc_feature
<222> LOCATION: (1)..(1085)
<223> OTHER INFORMATION: A chimeric transcriptional regulatory element,
      EXP-At.Act7/At.Tsf1/At.Tsf1

<400> SEQUENCE: 9
aattggccaa tctttgttct aaattgctaa taaacgacca tttccgtcaa ttctccttgg    60
ttgcaacagt ctacccgtca aatgtttact aatttataag tgtgaagttt gaattatgaa    120
agacgaaatc gtattaaaaa ttcacaagaa taaacaactc catagatttt caaaaaaaca    180
gtcacgagaa aaaaccaca gtccgtttgt ctgctcttct agttttatt atttttctat      240 taatagtttt ttgttatttc gagaataaaa tttgaacgat gtccgaacca caaagccga    300 gccgataaat cctaagccga gcctaacttt agccgtaacc atcagtcacg gctcccgggc    360
taattcattt gaaccgaatc ataatcaacg gtttagatca aactcaaaac aatctaacgg    420
caacatagac gcgtcggtga gctaaaaaga gtgtgaaagc caggtcacca tagcattgtc    480
tctcccagat ttttttatttg ggaaataata gaagaaatag aaaaaaataa aagagtgaga    540
aaaatcgtag agcggccgcg gaagtttctc tcttgaggga ggttgctcgt ggaatgggac    600
acatatggtt gttataataa accatttcca ttgtcatgag attttgaggt taatatatac    660
tttacttgtt cattatttta tttggtgttt gaataaatga tataaatggc tcttgataat    720
ctgcattcat tgagatatca aatatttact ctagagaaga gtgtcatata gattgatggt    780
ccacaatcaa tgaaattttt gggagacgaa catgtataac catttgcttg aataaccta    840 attaaaggt gtgattaaat gatgtttgta acatgtagta ctaaacattc ataaaacaca     900
accaacccaa gaggtattga gtattcacgg ctaaacaggg gcataatggt aatttaaaga    960
atgatatatt tttatgttaa accctaagct tggtttcgga ttcaacgcta taaataaaac    1020
cactctcgtt gctgattcca tttatcgttc ttattgaccc tagccgctac acactttct    1080 gcgat                                                                1085

<210> SEQ ID NO 10
<211> LENGTH: 553
<212> TYPE: DNA
<213> ORGANISM: Arabidopsis thaliana

<400> SEQUENCE: 10
aattggccaa tctttgttct aaattgctaa taaacgacca tttccgtcaa ttctccttgg    60
```

```
ttgcaacagt ctacccgtca aatgtttact aatttataag tgtgaagttt gaattatgaa      120
agacgaaatc gtattaaaaa ttcacaagaa taaacaactc catagatttt caaaaaaaca      180
gtcacgagaa aaaaccaca gtccgtttgt ctgctcttct agttttcatt attttctat       240
```

```
taatagtttt tgttatttc gagaataaaa tttgaacgat gtccgaacca caaaagccga       300
gccgataaat cctaagccga gcctaacttt agccgtaacc atcagtcacg gctcccgggc      360
taattcattt gaaccgaatc ataatcaacg gtttagatca aactcaaaac aatctaacgg      420
caacatagac gcgtcggtga gctaaaaaga gtgtgaaagc caggtcacca tagcattgtc      480
tctcccagat tttttatttg ggaaataata gaagaaatag aaaaaaataa aagagtgaga      540
aaaatcgtag agc                                                         553

<210> SEQ ID NO 11
<211> LENGTH: 427
<212> TYPE: DNA
<213> ORGANISM: Arabidopsis thaliana

<400> SEQUENCE: 11
ggaagtttct ctcttgaggg aggttgctcg tggaatggga cacatatggt tgttataata       60
aaccatttcc attgtcatga gattttgagg ttaatatata ctttacttgt tcattatttt      120
atttggtgtt tgaataaatg atataaatgg ctcttgataa tctgcattca ttgagatatc      180
aaatatttac tctagagaag agtgtcatat agattgatgg tccacaatca atgaaatttt      240
tgggagacga acatgtataa ccatttgctt gaataacctt aattaaaagg tgtgattaaa      300
tgatgtttgt aacatgtagt actaaacatt cataaaacac aaccaaccca agaggtattg      360
agtattcacg gctaaacagg ggcataatgg taatttaaag aatgatatta ttttatgtta      420
aaccccta                                                              427

<210> SEQ ID NO 12
<211> LENGTH: 49
<212> TYPE: DNA
<213> ORGANISM: Arabidopsis thaliana

<400> SEQUENCE: 12
tggtttcgga ttcaacgcta taaataaaac cactctcgtt gctgattcc                   49

<210> SEQ ID NO 13
<211> LENGTH: 621
<212> TYPE: DNA
<213> ORGANISM: Arabidopsis thaliana

<400> SEQUENCE: 13
atctctgagg taagcgttaa cgtacccta gatcgttctt tttcttttc gtctgctgat         60 cgttgctcat attatttcga tgattgttgg attcgatgct ctttgttgat tgatcgttct      120
gaaaattctg atctgttgtt tagattttat cgattgttaa tatcaacgtt tcactacttc      180
taaacgataa tttattcatg aaactatttt cccattctga tcgatcttgt tttgagattt      240
taatttgttc gattgattgt tggttggtgg atctatatac gagtgaactt gttgatttgc      300
gtatttaaga tgtatgtcga tttgaattgt gattgggtaa ttctggagta gcataacaaa      360
tccagtgttc cctttttcta agggtaattc tcggattgtt tgctttatat ctcttgaaat      420
tgccgatttg attgaattta gctcgcttag ctcagatgat agagcaccac aattttgtg       480 gtagaaatcg gtttgactcc gatagcggct ttttactatg attgttttgt gttaaagatg      540
```

```
attttcataa tggttatata tgtctactgt ttttattgat tcaatatttg attgttcttt    600
tttttgcaga tttgttgaca g                                              621
```

```
<210> SEQ ID NO 14
<211> LENGTH: 1092
<212> TYPE: DNA
<213> ORGANISM: Artificial sequence
<220> FEATURE:
<221> NAME/KEY: misc_feature
<222> LOCATION: (1)..(1092)
<223> OTHER INFORMATION: A chimeric transcriptional regulatory element,
      EXP-At.Tsf1/At.Act7/At.Tsf1

<400> SEQUENCE: 14
ggaagtttct ctcttgaggg aggttgctcg tggaatggga cacatatggt tgttataata     60
aaccatttcc attgtcatga gattttgagg ttaatatata ctttacttgt tcattatttt    120
atttggtgtt tgaataaatg atataaatgg ctcttgataa tctgcattca ttgagatatc    180
aaatatttac tctagagaag agtgtcatat agattgatgg tccacaatca atgaaatttt    240
tgggagacga acatgtataa ccatttgctt gaataacctt aattaaaagg tgtgattaaa    300
tgatgtttgt aacatgtagt actaaacatt cataaaacac aaccaaccca agaggtattg    360
agtattcacg gctaaacagg ggcataatgg taatttaaag aatgatatta ttttatgtta    420
aaccctaagc ttactagtca acaattggcc aatctttgtt ctaaattgct aataaacgac    480
catttccgtc aattctcctt ggttgcaaca gtctaccegt caaatgttta ctaatttata    540
agtgtgaagt ttgaattatg aaagacgaaa tcgtattaaa aattcacaag aataaacaac    600
tccatagatt ttcaaaaaaa cagtcacgag aaaaaaacca cagtccgttt gtctgctctt    660
ctagttttta ttatttttct attaatagtt ttttgttatt tcgagaataa atttgaacg     720 atgtccgaac cacaaaagcc gagccgataa atcctaagcc gagcctaact ttagccgtaa    780
ccatcagtca cggctcccgg gctaattcat ttgaaccgaa tcataatcaa cggtttagat    840
caaactcaaa aaaatctaac ggcaacatag acgcgtcggt gagctaaaaa gagtgtgaaa    900
gccaggtcac catagcattg tctctcccag attttttatt tgggaaataa tagaagaaat    960
agaaaaaaat aaaagagtga gaaaaatcgt agaagcttgg tttcggattc aacgctataa   1020
ataaaaccac tctcgttgct gattccattt atcgttctta ttgacctag ccgctacaca   1080 cttttctgcg at                                                       1092
```

```
<210> SEQ ID NO 15
<211> LENGTH: 551
<212> TYPE: DNA
<213> ORGANISM: Arabidopsis thaliana

<400> SEQUENCE: 15
aattggccaa tctttgttct aaattgctaa taaacgacca tttccgtcaa ttctccttgg     60
ttgcaacagt ctaccegtca aatgttact aattataag tgtgaagttt gaattatgaa    120
agacgaaatc gtattaaaaa ttcacaagaa taaacaactc catagatttt caaaaaaaca    180
gtcacgagaa aaaaccaca gtccgtttgt ctgctcttct agttttatt atttttctat     240 taatagtttt ttgttatttc gagaataaaa tttgaacgat gtccgaacca caaaagccga    300
gccgataaat cctaagccga gcctaacttt agccgtaacc atcagtcacg gctcccgggc    360
taattcattt gaaccgaatc ataatcaacg gtttagatca aactcaaaaa aatctaacgg    420
caacatagac gcgtcggtga gctaaaaaga gtgtgaaagc caggtcacca tagcattgtc    480
```

| | |
|---|---|
| tctcccagat tttttatttg ggaaataata gaagaaatag aaaaaaataa aagagtgaga | 540 |
| aaaatcgtag a | 551 |

<210> SEQ ID NO 16
<211> LENGTH: 1607
<212> TYPE: DNA
<213> ORGANISM: Arabidopsis thaliana

<400> SEQUENCE: 16

| | |
|---|---|
| ggtctgtata ccggggattg aagatgtaag tcatctcatt tactctcatc ttcaattcgt | 60 |
| aggaagtgaa aatgatagaa acaatcagag taatcatcat cacatttgta ggtagatgta | 120 |
| acggatatgg tggaaggtca ctcatcttac ctatggaaaa ctcaacaaat cctggaaaga | 180 |
| ctcgaactcg acaattctta ccctgttttt cgaaacactc tctaactaaa cccaacattt | 240 |
| attactagga ccatatccca ttttcaccca gtttcataga ctagattaac cctcatgact | 300 |
| gctgaatcag gtaaaacgaa acatcattgc ccttcttctc tcattttctc ctcatgtgcg | 360 |
| tatatattat acacttccac attcccacaa ttgtttacat gaaaacttcc ctcattttga | 420 |
| aaccctacat gttctaattt tttacccgaa aaaccatcg gagaaactat gttgaccaaa | 480 |
| aacaaacaaa catactatac atgttgacat aataaacgag cttttagtcc cttgttgtct | 540 |
| tattgaactt tcaacatatt tttgtagtta gttttacgtc gtcgccttta tactttggct | 600 |
| ttttcctagt tttctctctg tacggcgata gtagatgatg atgtacatgt tgataacatt | 660 |
| ggccctatct atcaattttt atatcaccca aattcacaga cgtacatgtg aaaactaaaa | 720 |
| ttttatactg tttcgcttgc tagaataata atatgcaaga aacgtacatg tgtgattgtg | 780 |
| tggttactgt tttttgagaa ttcaaaaaaa aaaaaaaatc atcttaaaca atcgaacttg | 840 |
| attaattcat aagccaacaa aattggaaaa aaatatttta gtttattta agtgttataa | 900 |
| aaaatttgat aattatttta gttattatat ttgaaaatag gtaaaataggg ttcttaatat | 960 |
| gtaacatgta catttttgca tatttctaat tcggtgtcat ccatacaaaa aacaaatggc | 1020 |
| aaaaatcaga atggatagag aattaatccg ctaaaatgta aatgttaggc ccaaattcgg | 1080 |
| cccattacac aaaaatctca gagggttaaa tacatcacct tctcgacgct aattcctcca | 1140 |
| ctacgtctct ctctcttgct ctccctcttc aagtcggctc ctttattgct acaggtttgt | 1200 |
| tgcttcttcg attcaattct tctttcgcct ccaattaggg tttgtttcga cctcaaatta | 1260 |
| tgcaactttg ggattatgtg attagaattt aaatttcggt gtttgtgaat ctaaatctag | 1320 |
| ttgattagca ttcttattgt tgttcatacg ttttaaccca atggttcgtc ttttagatct | 1380 |
| tctgttgtca tgatctggtt ttatgaaata gaaagtttcg ttttttgatga atcgttggtg | 1440 |
| ggttttccct tacttgatct gatctgatct gatctgatct ctctgcttta tatcagtgaa | 1500 |
| aaagtttcga gctttagaaa cagtggcggc tttccccaac ctcaactctg gctccggatt | 1560 |
| gaagaagctc ggtgagcatc ttctcactcg cagttacatc actgggt | 1607 |

<210> SEQ ID NO 17
<211> LENGTH: 1523
<212> TYPE: DNA
<213> ORGANISM: Arabidopsis thaliana

<400> SEQUENCE: 17

| | |
|---|---|
| ggtctgtata ccggggattg aagatgtaag tcatctcatt tactctcatc ttcaattcgt | 60 |
| aggaagtgaa aatgatagaa acaatcagag taatcatcat cacatttgta ggtagatgta | 120 |
| acggatatgg tggaaggtca ctcatcttac ctatggaaaa ctcaacaaat cctggaaaga | 180 |

```
ctcgaactcg acaattctta ccctgttttt cgaaacactc tctaactaaa cccaacattt    240
attactagga ccatatccca ttttcaccca gtttcataga ctagattaac cctcatgact    300
gctgaatcag gtaaaacgaa acatcattgc ccttcttctc tcattttctc ctcatgtgcg    360
tatatattat acacttccac attcccacaa ttgtttacat gaaaacttcc ctcattttga    420
aaccctacat gttctaattt tttacccgaa aaaccatcg gagaaactat gttgaccaaa      480
aacaaacaaa catactatac atgttgacat aataaacgag cttttagtcc cttgttgtct    540
tattgaactt tcaacatatt tttgtagtta gttttacgtc gtcgccttta tactttggct    600
ttttcctagt tttctctctg tacggcgata gtagatgatg atgtacatgt tgataacatt    660
ggccctatct atcaattttt atatcaccca aattcacaga cgtacatgtg aaaactaaaa    720
ttttatactg tttcgcttgc tagaataata atatgcaaga aacgtacatg tgtgattgtg    780
tggttactgt tttttgagaa ttcaaaaaaa aaaaaaatc atcttaaaca atcgaacttg    840
attaattcat aagccaacaa aattggaaaa aaatatttta gttatttta agtgttataa    900 aaaatttgat aattatttta gttattatat ttgaaaatag gtaaaatagg ttcttaatat    960
gtaacatgta cattttgca tatttctaat tcggtgtcat ccatacaaaa aacaaatggc    1020
aaaaatcaga atggatagag aattaatccg ctaaaatgta aatgttaggc ccaaattcgg    1080
cccattacac aaaaatctca gagggttaaa tacatcacct tctcgacgct aattcctcca    1140
ctacgtctct ctctcttgct ctccctcttc aagtcggctc ctttattgct acaggtttgt    1200
tgcttcttcg attcaattct tctttcgcct ccaattaggg tttgtttcga cctcaaatta    1260
tgcaactttg ggattatgtg attagaattt aaatttcggt gtttgtgaat ctaaatctag    1320
ttgattagca ttcttattgt tgttcatacg ttttaaccca atggttcgtc ttttagatct    1380
tctgttgtca tgatctggtt ttatgaaata gaaagtttcg ttttttgatga atcgttggtg    1440 ggttttcct tacttgatct gatctgatct gatctgatct ctctgcttta tatcagtgaa    1500
aaagtttcga gctttagaaa cag                                            1523
```

<210> SEQ ID NO 18
<211> LENGTH: 84
<212> TYPE: DNA
<213> ORGANISM: Arabidopsis thaliana

<400> SEQUENCE: 18

```
tggcggcttt ccccaacctc aactctggct ccggattgaa gaagctcggt gagcatcttc     60
tcactcgcag ttacatcact gggt                                            84
```

<210> SEQ ID NO 19
<211> LENGTH: 100
<212> TYPE: DNA
<213> ORGANISM: Arabidopsis thaliana

<400> SEQUENCE: 19

```
tagaatctgt tttctaaggg ctgtctcaat tatctatctt gttttgaaac aatagtagta     60
accattactt tcttctgtct ctctatgtat gtatgtttat                           100
```

<210> SEQ ID NO 20
<211> LENGTH: 617
<212> TYPE: DNA
<213> ORGANISM: Artificial sequence
<220> FEATURE:
<221> NAME/KEY: misc_feature
<222> LOCATION: (1)..(617)

<223> OTHER INFORMATION: A chimeric transcriptional regulatory element,
     EXP-At.Tsf1/Nt.eIF-4A10

<400> SEQUENCE: 20

```
ggaagtttct ctcttgaggg aggttgctcg tggaatggga cacatatggt tgttataata      60
aaccatttcc attgtcatga gattttgagg ttaatatata ctttacttgt tcattatttt     120
atttggtgtt tgaataaatg atataaatgg ctcttgataa tctgcattca ttgagatatc     180
aaatatttac tctagagaag agtgtcatat agattgatgg tccacaatca atgaaatttt     240
tgggagacga acatgtataa ccatttgctt gaataacctt aattaaaagg tgtgattaaa     300
tgatgtttgt aacatgtagt actaaacatt cataaaacac aaccaaccca agaggtattg     360
agtattcacg gctaaacagg ggcataatgg taatttaaag aatgatatta ttttatgtta     420
aaccctaagc ttaaacagta ttcagaaaga ccataaaaaa acactagtct caatctttct     480
cttttcctct ttcctgaact cctgcggcgt agatccgagg agtttcagac aaaaccctaa     540
ccccccaatc gcttttaccc acttttcatt tcactctctc tttcctattc ctcagatctt     600
ttcctcatct ctatcag                                                    617
```

<210> SEQ ID NO 21
<211> LENGTH: 91
<212> TYPE: DNA
<213> ORGANISM: Nicotiana tabacum

<400> SEQUENCE: 21

```
aaacagtatt cagaaagacc ataaaaaaac actagtctca atctttctct tttcctcttt      60
cctgaactcc tgcggcgtag atccgaggag t                                     91
```

<210> SEQ ID NO 22
<211> LENGTH: 94
<212> TYPE: DNA
<213> ORGANISM: Nicotiana tabacum

<400> SEQUENCE: 22

```
ttcagacaaa accctaaccc cccaatcgct tttacccact tttcatttca ctctctcttt      60
cctattcctc agatcttttc ctcatctcta tcag                                  94
```

<210> SEQ ID NO 23
<211> LENGTH: 892
<212> TYPE: DNA
<213> ORGANISM: Nicotiana tabacum

<400> SEQUENCE: 23

```
gttagctatg ttttttttcc ctttaatatt ttaatgtatt tcttgtaata tttgtttgtg      60
tattgaagat tgaatcttga tgattgattg ttggtctgac tacagctggg ttttgtgtta     120
tgtaactatt tttaactatt ttggatagag gtctgtttga tgtgatgttc ttgattataa     180
aaataccatc ctactttgtt atctcatatc tggttggaac atgagcaatt tcatttctcc     240
tagttcttga attaaaaacc tgaaagtatt gtgcaaaaag atgctaggaa tgagactatc     300
attgttttga tgcaatatgt tcttttaagt aataggtgtt ttgtaagaag tctacgcagt     360
tctggatgta ttttactact cgggaaaact ggatagttgg atacttatta tgtataggaa     420
gtaaatgtgg ggattataat gcctttctct gccatctgct ctttgtattt tgtgtaacgc     480
ttggcatgcc tctcgtcaga tagccatcgc taccgtacat tcttttaaga atgaagcact     540
tagacacttg ctcgtttctg cctttgtcac attgacccag catcatataa tctgaaagat     600
```

```
tggttagcag ttggctgcta tttaacttgt atgttaaaac aattgatttt catgtgtatc      660
tcctcctttt gtgctttgtg cttcttcata aagaaagaa acatacatt cggttgtgct       720 ctcctccttt ttcaatggta gagaggaaga acagataatt ttattgctgc tgtaggtatt    780
tgacatctgt gatattttca tagtaaggtt ttgtttttc cttttatt agttcaagat       840 tgtttcatga atttccataa gcgtaatacc atagttcttt tatttgctac ag            892
```

```
<210> SEQ ID NO 24
<211> LENGTH: 573
<212> TYPE: DNA
<213> ORGANISM: Artificial sequence
<220> FEATURE:
<221> NAME/KEY: misc_feature
<222> LOCATION: (1)..(573)
<223> OTHER INFORMATION: A chimeric transcriptional regulatory element,
      EXP-At.Tsf1/At.EF1beta

<400> SEQUENCE: 24
```

```
ggaagtttct ctcttgaggg aggttgctcg tggaatggga cacatatggt tgttataata    60
aaccatttcc attgtcatga gattttgagg ttaatatata ctttacttgt tcattatttt   120
atttggtgtt tgaataaatg atataaatg ctcttgataa tctgcattca ttgagatatc   180
aaatatttac tctagagaag agtgtcatat agattgatgg tccacaatca atgaaatttt   240
tgggagacga acatgtataa ccatttgctt gaataacctt aattaaaagg tgtgattaaa   300
tgatgtttgt aacatgtagt actaaacatt cataaaacac aaccaaccca agaggtattg   360
agtattcacg gctaaacagg ggcataatgg taatttaaag aatgatatta ttttatgtta   420
aaccctaagc ttatctgatc tgatctctct gctttatatc agtgaaaaag tttcgagctt   480
tagaaacagt ggcggctttc cccaacctca actctggctc cggattgaag aagctcggtg   540
agcatcttct cactcgcagt tacatcactg ggt                                  573
```

```
<210> SEQ ID NO 25
<211> LENGTH: 57
<212> TYPE: DNA
<213> ORGANISM: Arabidopsis thaliana

<400> SEQUENCE: 25
```

```
atctgatctg atctctctgc tttatatcag tgaaaaagtt tcgagcttta gaaacag        57
```

```
<210> SEQ ID NO 26
<211> LENGTH: 562
<212> TYPE: DNA
<213> ORGANISM: Artificial sequence
<220> FEATURE:
<221> NAME/KEY: misc_feature
<222> LOCATION: (1)..(562)
<223> OTHER INFORMATION: A chimeric transcriptional regulatory element,
      EXP-At.Tsf1/At.Act7

<400> SEQUENCE: 26
```

```
ggaagtttct ctcttgaggg aggttgctcg tggaatggga cacatatggt tgttataata    60
aaccatttcc attgtcatga gattttgagg ttaatatata ctttacttgt tcattatttt   120
atttggtgtt tgaataaatg atataaatg ctcttgataa tctgcattca ttgagatatc   180
aaatatttac tctagagaag agtgtcatat agattgatgg tccacaatca atgaaatttt   240
tgggagacga acatgtataa ccatttgctt gaataacctt aattaaaagg tgtgattaaa   300
tgatgtttgt aacatgtagt actaaacatt cataaaacac aaccaaccca agaggtattg   360
agtattcacg gctaaacagg ggcataatgg taatttaaag aatgatatta ttttatgtta   420
```

```
aaccctaagc ttatatattc gcacatgtac tcgtttcgct ttccttagtg ttagctgctg    480
ccgctgttgt ttctcctcca tttctctatc tttctctctc gctgcttctc gaatcttctg    540
tatcatcttc ttcttcttca ag                                             562
```

<210> SEQ ID NO 27
<211> LENGTH: 37
<212> TYPE: DNA
<213> ORGANISM: Arabidopsis thaliana

<400> SEQUENCE: 27

```
tatatattcg cacatgtact cgtttcgctt tccttag                              37
```

<210> SEQ ID NO 28
<211> LENGTH: 669
<212> TYPE: DNA
<213> ORGANISM: Artificial sequence
<220> FEATURE:
<221> NAME/KEY: misc_feature
<222> LOCATION: (1)..(669)
<223> OTHER INFORMATION: A chimeric transcriptional regulatory element,
      EXP-At.Tsf1/At.enr-A

<400> SEQUENCE: 28

```
ggaagtttct ctcttgaggg aggttgctcg tggaatggga cacatatggt tgttataata     60
aaccatttcc attgtcatga gattttgagg ttaatatata ctttacttgt tcattatttt    120
atttggtgtt tgaataaatg atataaatgg ctcttgataa tctgcattca ttgagatatc    180
aaatatttac tctagagaag agtgtcatat agattgatgg tccacaatca atgaaatttt    240
tgggagacga acatgtataa ccatttgctt gaataacctt aattaaaagg tgtgattaaa    300
tgatgtttgt aacatgtagt actaaacatt cataaaacac aaccaaccca agaggtattg    360
agtattcacg gctaaacagg ggcataatgg taatttaaag aatgatatta ttttatgtta    420
aaccctaagc ttgagaagag aaaaagtcga aaattcagaa acggtttaaa gttaaccagg    480
attccggttt ttataacaga accgatcggt tttgtaattg agacgaaaac ttctgatatc    540
acttaaaaac ttcacagaaa caacacctcg atctcatcga agctcctctc tcttacatat    600
catcacttca catcaaccaa acctacttct gtctctctct ctcgctctct atctctcacg    660
ctctcacag                                                            669
```

<210> SEQ ID NO 29
<211> LENGTH: 77
<212> TYPE: DNA
<213> ORGANISM: Arabidopsis thaliana

<400> SEQUENCE: 29

```
tgagaagaga aaaagtcgaa aattcagaaa cggtttaaag ttaaccagga ttccggtttt     60
tataacagaa ccgatcg                                                    77
```

<210> SEQ ID NO 30
<211> LENGTH: 161
<212> TYPE: DNA
<213> ORGANISM: Arabidopsis thaliana

<400> SEQUENCE: 30

```
gttttgtaat tgagacgaaa acttctgata tcacttaaaa acttcacaga acaacacct      60 cgatctcatc gaagctcctc tctcttacat atcatcactt cacatcaacc aaacctactt    120
ctgtctctct ctctcgctct ctatctctca cgctctcaca g                        161
```

<210> SEQ ID NO 31
<211> LENGTH: 467
<212> TYPE: DNA
<213> ORGANISM: Arabidopsis thaliana

<400> SEQUENCE: 31

| | | | | | | |
|---|---|---|---|---|---|---|
| gtttttttct | ctctctgtct | ctctcttgtt | ctccatttgc | gtctctgttt | gtttgatgag | 60 |
| tttctgaatg | ttaaatgcag | atgtgttttg | gttttctgtg | gaagtttta | tatctctgtt | 120 |
| gattgagttt | ttctctgatg | ttgttgggct | ccaaaaaatt | cgaaacttgt | attatctctc | 180 |
| gtttaggttt | cgtgttctct | gcattgatct | gcttctttaa | tttgttaact | atactcacgt | 240 |
| atgtgaaaaa | tctgaacttt | gtttgttaac | tctaatccaa | atcattagaa | aaatgcagat | 300 |
| tgagatttct | ctaatgcagt | gcttgaaatt | ttggaaacta | gggttcttgt | tataatgttt | 360 |
| caagtagtga | acttatgtca | acttgtgctt | taggtttgat | ctgattctta | aattttgttt | 420 |
| catatgtggt | ctttcttaca | atgtttctgg | atttgttgtt | ttagtag | | 467 |

<210> SEQ ID NO 32
<211> LENGTH: 1242
<212> TYPE: DNA
<213> ORGANISM: Nicotiana tabacum

<400> SEQUENCE: 32

| | | | | | | |
|---|---|---|---|---|---|---|
| atcatgtata | tttgtgcata | tccatgaaaa | tttgtgttat | atatacgata | tataatgtga | 60 |
| tacacatagg | cgtccataaa | agaattgtgt | tgtatacacg | atatacaaag | tgatatacag | 120 |
| atgtccttaa | aaatatgtgt | gtgatataca | ttgatgtaca | caatatgcaa | cgcgatatac | 180 |
| acatgtcaca | gttggatttt | aggtctgatg | ttttacatga | aatcagtcta | aatcacttct | 240 |
| aatcttgctc | aaattttgta | tatagccccg | tttaggtatt | ttcaaccaat | ttcactcaca | 300 |
| ccactcgttc | aatctaacca | aaaaaaagaa | gagagaagaa | aaacaaagtt | gaaatgaatt | 360 |
| tttctctctt | agtttttgct | tataattttt | ctgattacct | tttcaccccca | ctgattttt | 420 |
| ttgcataatt | tgcaaggatt | tttgctaaac | tatgagagcg | aaagaaaaga | gatagaagaa | 480 |
| gaaatacaag | gagagaaagg | gggagggacg | cagtgaacaa | aaaaagaagt | tagcggcgaa | 540 |
| gagggggggg | ggggggaagc | agacggtttg | gggccaattg | tttgagagag | aatatataag | 600 |
| agagtagttt | ttttaggatt | tggctatata | atgtcaatt | tttggggcta | tcttttccta | 660 |
| acctaatata | agactaaaaa | attgtcaatt | cctgttatgt | gttatcacct | ggtgccattt | 720 |
| tctcatagtt | atacatatag | tgaaaggaaa | agagggtatt | agtgccaatt | ttgtaaagag | 780 |
| gttagaccta | aattaggccc | aagaggccca | atagaaaatc | tagccctcaa | ttttgtggaa | 840 |
| tccacgtcac | cgacttcttg | cattaccacc | cgaagcggct | ccgtattgat | cctgtaactc | 900 |
| ccaatttcgg | gtcaaaatag | gaatttcaaa | tacagaagcc | aaaaaaaaaa | ggaaagtaat | 960 |
| ccaaaacagt | attcagaaag | accataaaaa | aacactagtc | tcaatctttc | tcttttcctc | 1020 |
| tttcctgaac | tcctgcggcg | tagatccgag | gagtttcaga | caaaccccta | accccccaat | 1080 |
| cgcttttacc | cacttttcat | ttcactctct | ctttcctatt | cctcagatct | tttcctcatc | 1140 |
| tctatcagtt | cagacaaaac | cctaaccccc | caatcgcttt | tacccacttt | tcatttcact | 1200 |
| ctctctttcc | tattcctcag | atcttttcct | catctctatc | ag | | 1242 |

<210> SEQ ID NO 33
<211> LENGTH: 1054
<212> TYPE: DNA

<213> ORGANISM: Nicotiana tabacum

<400> SEQUENCE: 33

```
atcatgtata tttgtgcata tccatgaaaa tttgtgttat atatacgata tataatgtga        60
tacacatagg cgtccataaa agaattgtgt tgtatacacg atatacaaag tgatatacag       120
atgtccttaa aaatatgtgt gtgatataca ttgatgtaca caatatgcaa cgcgatatac       180
acatgtcaca gttggatttt aggtctgatg ttttacatga aatcagtcta aatcacttct       240
aatcttgctc aaattttgta tatagccccg tttaggtatt tcaaccaat ttcactcaca        300
ccactcgttc aatctaacca aaaaaaagaa gagagaagaa aaacaaagtt gaaatgaatt       360
tttctctctt agtttttgct tataattttt ctgattacct tttcacccca ctgatttttt       420
ttgcataatt tgcaaggatt tttgctaaac tatgagagcg aaagaaaaga gatagaagaa       480
gaaatacaag gagagaaagg gggagggacg cagtgaacaa aaaagaagt tagcggcgaa        540
gagggggggg gggggaagc agacggttttg gggccaattg tttgagagag aatatataag       600
agagtagttt tttaggatt tggctatata atgtcaattt tttggggcta tcttttccta        660
acctaatata agactaaaaa attgtcaatt cctgttatgt gttatcaccc ggtgccattt       720
tctcatagtt atacatatag tgaaggaaa agagggtatt agtgccaatt ttgtaaagag        780
gttagaccta aattaggccc aagaggccca atagaaaatc tagccctcaa ttttgtggaa       840
tccacgtcac cgacttcttg cattaccacc cgaagcggct ccgtattgat cctgtaactc       900
ccaattcgg gtcaaaatag gaatttcaaa tacagaagcc aaaaaaaaaa ggaaagtaat        960
ccaaaacagt attcagaaag accataaaaa aacactagtc tcaatctttc tcttttcctc      1020
tttcctgaac tcctgcggcg tagatccgag gagt                                   1054
```

<210> SEQ ID NO 34
<211> LENGTH: 892
<212> TYPE: DNA
<213> ORGANISM: Nicotiana tabacum

<400> SEQUENCE: 34

```
gttagctatg tttttttcc ctttaatatt ttaatgtatt tcttgtaata tttgtttgtg         60
tattgaagat tgaatcttga tgattgattg ttggtctgac tacagctggg ttttgtgtta       120
tgtaactatt tttaactatt ttggatagag gtctgtttga tgtgatgttc ttgattataa       180
aaataccatc ctactttgtt atctcatatc tggttggaac atgagcaatt tcatttctcc       240
tagttcttga attaaaaacc tgaaagtatt gtgcaaaaag atgctaggaa tgagactatc       300
attgttttga tgcaatatgt tctttaagt aataggtgtt ttgtaagaag tctacgcagt        360
tctggatgta ttttactact cgggaaaact ggatagttgg atacttatta tgtataggaa       420
gtaaatgtgg ggattataat gcctttctct gccatctgct ctttgtattt tgtgtaaagc       480
ttggcatgcc tctcgtcaga tagccatcgc taccgtacat tcttttaaga atgaagcact       540
tagacacttg ctcgtttctg cctttgtcac attgacccag catcatataa tctgaaagat       600
tggttagcag ttggctgcta tttaacttgt atgttaaaac aattgatttt catgtgtatc       660
tcctcctttt gtgctttgtg cttcttcata aaagaaagaa aacatacatt cggttgtgct       720
ctcctccttt ttcaatggta gagaggaaga acagataatt ttattgctgc tgtaggtatt       780
tgacatctgt gatattttca tagtaaggtt ttgtttttc ctttttattt agttcaagat       840
tgtttcatga atttccataa gcgtaatacc atagttcttt tatttgctac ag               892
```

```
<210> SEQ ID NO 35
<211> LENGTH: 1712
<212> TYPE: DNA
<213> ORGANISM: Artificial sequence
<220> FEATURE:
<221> NAME/KEY: misc_feature
<222> LOCATION: (1)..(1712)
<223> OTHER INFORMATION: A chimeric transcriptional regulatory element,
      EXP-At.Act7/Nt.elF4A10

<400> SEQUENCE: 35
```

| | | | | |
|---|---|---|---|---|
| aattggccaa tctttgttct aaattgctaa taaacgacca tttccgtcaa ttctccttgg | | | | 60 |
| ttgcaacagt ctacccgtca aatgtttact aatttataag tgtgaagttt gaattatgaa | | | | 120 |
| agacgaaatc gtattaaaaa ttcacaagaa taaacaactc catagatttt caaaaaaaca | | | | 180 |
| gtcacgagaa aaaaaccaca gtccgtttgt ctgctcttct agtttttatt attttttctat | | | | 240 |
| taatagttttt ttgttattttc gagaataaaa tttgaacgat gtccgaacca caaaagccga | | | | 300 |
| gccgataaat cctaagccga gcctaacttt agccgtaacc atcagtcacg gctcccgggc | | | | 360 |
| taattcatttt gaaccgaatc ataatcaacg gtttagatca aactcaaaac aatctaacgg | | | | 420 |
| caacatagac gcgtcggtga gctaaaaaga gtgtgaaagc caggtcacca tagcattgtc | | | | 480 |
| tctcccagat tttttatttg ggaaataata gaagaaatag aaaaaaataa aagagtgaga | | | | 540 |
| aaaatcgtag agctgtcggc cgcatcatgt atatttgtgc atatccatga aaatttgtgt | | | | 600 |
| tatatatacg atatataatg tgatacacat aggcgtccat aaaagaattg tgttgtatac | | | | 660 |
| acgatataca aagtgatata cagatgtcct taaaaatatg tgtgtgatat acattgatgt | | | | 720 |
| acacaatatg caacgcgata tacacatgtc acagttggat tttaggtctg atgttttaca | | | | 780 |
| tgaaatcagt ctaaatcact tctaatcttg ctcaaatttt gtatatagcc ccgtttaggt | | | | 840 |
| attttcaacc aatttcactc acaccactcg ttcaatctaa ccaaaaaaaa gaagagagaa | | | | 900 |
| gaaaacaaa gttgaaatga atttttctct cttagttttt gcttataatt tttctgatta | | | | 960 |
| ccttttcacc ccactgattt tttttgcata atttgcaagg attttttgcta aactatgaga | | | | 1020 |
| gcgaaagaaa agagatagaa gaagaaaata caaggagaga aaggggggagg gacgcagtga | | | | 1080 |
| acaaaaaaag aagttagcgg cgaagagggg gggggggggg aagcagacgg tttgggccca | | | | 1140 |
| attgtttgag agagaatata taagagagta gtttttttag gatttggcta tataatgtca | | | | 1200 |
| attttttggg gctatctttt cctaacctaa tataagacta aaaaattgtc aattcctgtt | | | | 1260 |
| atgtgttatc acctggtgcc attttctcat agttatacat atagtgaaag gaaaagaggg | | | | 1320 |
| tattagtgcc aattttgtaa agaggttaga cctaaattag gcccaagagg cccaatagaa | | | | 1380 |
| aatctagccc tcaattttgt ggaatccacg tcaccgactt cttgcattac cacccgaagc | | | | 1440 |
| ggctccgtat tgatcctgta actcccaatt tcgggtcaaa ataggaattt caaatacaga | | | | 1500 |
| agccaaaaaa aaaaggaaag taatccaaaa cagtattcag aaagaccata aaaaaacact | | | | 1560 |
| agtctcaatc cttctctttt cctctttcct gaactcctgc ggcgtagatc cgaggagttt | | | | 1620 |
| cagacaaaac cctaaccccc caatcgcttt tacccacttt tcatttcact atctctttcc | | | | 1680 |
| tattcctcag atcttttcct catctctatc ag | | | | 1712 |

```
<210> SEQ ID NO 36
<211> LENGTH: 1055
<212> TYPE: DNA
<213> ORGANISM: Nicotiana tabacum

<400> SEQUENCE: 36
```

| | | | | |
|---|---|---|---|---|
| atcatgtata tttgtgcata tccatgaaaa tttgtgttat atatacgata tataatgtga | | | | 60 |

```
tacacatagg cgtccataaa agaattgtgt tgtatacacg atatacaaag tgatatacag      120
atgtccttaa aaatatgtgt gtgatataca ttgatgtaca caatatgcaa cgcgatatac      180
acatgtcaca gttggatttt aggtctgatg ttttacatga aatcagtcta aatcacttct      240
aatcttgctc aaattttgta tatagccccg tttaggtatt ttcaaccaat ttcactcaca      300
ccactcgttc aatctaacca aaaaaaagaa gagagaagaa aaacaaagtt gaaatgaatt      360
tttctctctt agttttgct tataatttt ctgattacct tttcacccca ctgatttttt       420
ttgcataatt tgcaaggatt tttgctaaac tatgagagcg aaagaaaaga gatagaagaa      480
gaaaatacaa ggagagaaag ggggagggac gcagtgaaca aaaaaagaag ttagcggcga      540 agagggggg ggggggaag cagacggttt ggggccaatt gtttgagaga gaatatataa        600
gagagtagtt ttttaggat ttggctatat aatgtcaatt ttttgggct atctttcct         660 aacctaatat aagactaaaa aattgtcaat tcctgttatg tgttatcacc tggtgccatt      720
ttctcatagt tatacatata gtgaaaggaa aagagggtat tagtgccaat tttgtaaaga     780
ggttagacct aaattaggcc caagaggccc aatagaaaat ctagccctca attttgtgga    840
atccacgtca ccgacttctt gcattaccac ccgaagcggc tccgtattga tcctgtaact    900
cccaatttcg ggtcaaaata ggaatttcaa atacagaagc caaaaaaaaa aggaaagtaa    960
tccaaaacag tattcagaaa gaccataaaa aaacactagt ctcaatcctt ctcttttcct   1020
ctttcctgaa ctcctgcggc gtagatccga ggagt                               1055

<210> SEQ ID NO 37
<211> LENGTH: 94
<212> TYPE: DNA
<213> ORGANISM: Nicotiana tabacum

<400> SEQUENCE: 37
ttcagacaaa accctaaccc cccaatcgct tttacccact tttcatttca ctatctcttt       60
cctattcctc agatcttttc ctcatctcta tcag                                   94

<210> SEQ ID NO 38
<211> LENGTH: 644
<212> TYPE: DNA
<213> ORGANISM: Artificial sequence
<220> FEATURE:
<221> NAME/KEY: misc_feature
<222> LOCATION: (1)..(644)
<223> OTHER INFORMATION: A chimeric transcriptional regulatory element,
      EXP-FMV/Ph.DnaK

<400> SEQUENCE: 38
gcattccaga ttgggttcaa tcaacaaggt acgagccata tcactttatt caaattggta       60
tcgccaaaac caagaaggaa ctcccatcct caaaggtttg taaggaagaa ttctcagtcc      120
aaagcctcaa caaggtcagg gtacagagtc tccaaaccat tagccaaaag ctacaggaga      180
tcaatgaaga atcttcaatc aaagtaaact actgttccag cacatgcatc atggtcagta      240
agtttcagaa aaagacatcc accgaagact taaagttagt gggcatcttt gaaagtaatc      300
ttgtcaacat cgagcagctg gcttgtgggg accagacaaa aaaggaatgg tgcagaattg      360
ttaggcgcac ctaccaaaag catctttgcc tttattgcaa agataaagca gattcctcta      420
gtacaagtgg ggaacaaaat aacgtggaaa agagctgtcc tgacagccca ctcactaatg      480
cgtatgacga acgcagtgac gaccacaaaa gaattccctc tatataagaa ggcattcatt      540
cccatttgaa ggacacagaa aaatttgcta cattgtttca caaacttcaa atattattca      600
```

```
tttatttgtc agctttcaaa ctctttgttt cttgtttgtt gatt            644
```

<210> SEQ ID NO 39
<211> LENGTH: 552
<212> TYPE: DNA
<213> ORGANISM: Figwort mosaic virus

<400> SEQUENCE: 39

```
gcattccaga ttgggttcaa tcaacaaggt acgagccata tcactttatt caaattggta    60
tcgccaaaac caagaaggaa ctcccatcct caaaggtttg taaggaagaa ttctcagtcc   120
aaagcctcaa caaggtcagg gtacagagtc tccaaaccat tagccaaaag ctacaggaga   180
tcaatgaaga atcttcaatc aaagtaaact actgttccag cacatgcatc atggtcagta   240
agtttcagaa aaagacatcc accgaagact aaagttagt gggcatcttt gaaagtaatc    300
ttgtcaacat cgagcagctg gcttgtgggg accagacaaa aaggaatgg tgcagaattg    360
ttaggcgcac ctaccaaaag catctttgcc tttattgcaa agataaagca gattcctcta   420
gtacaagtgg ggaacaaaat aacgtggaaa agagctgtcc tgacagccca ctcactaatg   480
cgtatgacga acgcagtgac gaccacaaaa gaattccctc tatataagaa ggcattcatt   540
cccatttgaa gg                                                       552
```

<210> SEQ ID NO 40
<211> LENGTH: 89
<212> TYPE: DNA
<213> ORGANISM: Petunia hybrida

<400> SEQUENCE: 40

```
cagaaaaatt tgctacattg tttcacaaac ttcaaatatt attcatttat ttgtcagctt    60
tcaaactctt tgtttcttgt tgttgatt                                       89
```

<210> SEQ ID NO 41
<211> LENGTH: 1085
<212> TYPE: DNA
<213> ORGANISM: Artificial sequence
<220> FEATURE:
<221> NAME/KEY: misc_feature
<222> LOCATION: (1)..(1085)
<223> OTHER INFORMATION: A chimeric transcriptional regulatory element,
      EXP-At.Act7/At.Tsf1

<400> SEQUENCE: 41

```
aattggccaa tctttgttct aaattgctaa taaacgacca tttccgtcaa ttctccttgg    60
ttgcaacagt ctacccgtca aatgtttact aatttataag tgtgaagttt gaattatgaa   120
agacgaaatc gtattaaaaa ttcacaagaa taaacaactc catagatttt caaaaaaaca   180
gtcacgagaa aaaaccaca gtccgtttgt ctgctcttct agtttttatt attttttctat   240
taatagtttt tgttattc gagaataaaa tttgaacgat gtccgaacca caaaagccga    300
gccgataaat cctaagccga gcctaacttt agccgtaacc atcagtcacg gctcccgggc   360
taattcattt gaaccgaatc ataatcaacg gtttagatca aactcaaaac aatctaacgg   420
caacatagac gcgtcggtga gctaaaaaga gtgtgaaagc caggtcacca tagcattgtc   480
tctcccagat ttttttattg ggaaataata gaagaaatag aaaaaaataa aagagtgaga   540
aaatcgtag agcggccgcg gaagtttctc tcttgaggga ggttgctcgt ggaatgggac   600
acatatggtt gttataataa accatttcca ttgtcatgag attttgaggt taatatatac   660
tttacttgtt cattattttta tttggtgttt gaataaatga tataaatggc tcttgataat   720
```

```
ctgcattcat tgagatatca aatatttact ctagagaaga gtgtcatata gattgatggt      780
ccacaatcaa tgaaattttt gggagacgaa catgtataac catttgcttg ataacctta       840 attaaaaggt gtgattaaat gatgtttgta acatgtagta ctaaacattc ataaaacaca      900
accaacccaa gaggtattga gtattcacgg ctaaacaggg gcataatggt aatttaaaga      960
atgatattat tttatgttaa accctaagct tggtttcgga ttcaacgcta taaataaaac     1020
cactctcgtt gctgattcca tttatcgttc ttattgaccc tagccgctac acactttct      1080 gcgat                                                                 1085
```

<210> SEQ ID NO 42
<211> LENGTH: 480
<212> TYPE: DNA
<213> ORGANISM: Arabidopsis thaliana

<400> SEQUENCE: 42

```
ggaagtttct ctcttgaggg aggttgctcg tggaatggga cacatatggt tgttataata       60
aaccatttcc attgtcatga gattttgagg ttaatatata ctttacttgt tcattatttt      120
atttggtgtt tgaataaatg atataaatgg ctcttgataa tctgcattca ttgagatatc      180
aaatatttac tctagagaag agtgtcatat agattgatgg tccacaatca atgaaatttt      240
tgggagacga acatgtataa ccatttgctt gaataacctt aattaaaagg tgtgattaaa      300
tgatgtttgt aacatgtagt actaaacatt cataaaacac aaccaaccca agaggtattg      360
agtattcacg gctaaacagg gcataatgg taatttaaag aatgatatta ttttatgtta      420
aaccctaagc ttggtttcgg attcaacgct ataaataaaa ccactctcgt tgctgattcc      480
```

<210> SEQ ID NO 43
<211> LENGTH: 643
<212> TYPE: DNA
<213> ORGANISM: Pisum sativum

<400> SEQUENCE: 43

```
agctttcgtt cgtatcatcg gtttcgacaa cgttcgtcaa gttcaatgca tcagtttcat       60
tgcgcacaca ccagaatcct actgagttcg agtattatgg cattgggaaa actgtttttc      120
ttgtaccatt tgttgtgctt gtaatttact gtgttttta ttcggttttc gctatcgaac       180
tgtgaaatgg aaatggatgg agaagagtta atgaatgata tggtcctttt gttcattctc      240
aaattaatat tatttgtttt ttctcttatt tgttgtgtgt tgaatttgaa attataagag      300
atatgcaaac attttgtttt gagtaaaaat gtgtcaaatc gtggcctcta atgaccgaag      360
ttaatatgag gagtaaaaca cttgtagttg taccattatg cttattcact aggcaacaaa      420
tatattttca gacctagaaa agctgcaaat gttactgaat acaagtatgt cctcttgtgt      480
tttagacatt tatgaacttt cctttatgta attttccaga atccttgtca gattctaatc      540
attgctttat aattatagtt atactcatgg atttgtagtt gagtatgaaa atattttta       600 atgcatttta tgacttgcca attgattgac aacatgcatc aat                       643
```

<210> SEQ ID NO 44
<211> LENGTH: 253
<212> TYPE: DNA
<213> ORGANISM: Agrobacterium tumefaciens

<400> SEQUENCE: 44

```
gatcgttcaa acatttggca ataaagtttc ttaagattga atcctgttgc cggtcttgcg       60
```

```
atgattatca tataatttct gttgaattac gttaagcatg taataattaa catgtaatgc      120
atgacgttat ttatgagatg ggtttttatg attagagtcc cgcaattata catttaatac      180
gcgatagaaa acaaaatata gcgcgcaaac taggataaat tatcgcgcgc ggtgtcatct      240
atgttactag atc                                                        253
```

<210> SEQ ID NO 45
<211> LENGTH: 1046
<212> TYPE: DNA
<213> ORGANISM: artificial sequence
<220> FEATURE:
<221> NAME/KEY: misc_feature
<222> LOCATION: (1)..(1046)
<223> OTHER INFORMATION: chimeric promoter of linked AtTsf1 promoter and
      AtAct7 enhancer

<400> SEQUENCE: 45

```
ggaagtttct ctcttgaggg aggttgctcg tggaatggga cacatatggt tgttataata       60
aaccatttcc attgtcatga gattttgagg ttaatatata ctttacttgt tcattatttt      120
atttggtgtt tgaataaatg atataaatgg ctcttgataa tctgcattca ttgagatatc      180
aaatatttac tctagagaag agtgtcatat agattgatgg tccacaatca atgaaatttt      240
tgggagacga acatgtataa ccatttgctt gaataacctt aattaaaagg tgtgattaaa      300
tgatgtttgt aacatgtagt actaaacatt cataaaacac aaccaaccca agaggtattg      360
agtattcacg gctaaacagg ggcataatgg taatttaaag aatgatatta ttttatgtta      420
aaccctaagc ttactagtca acaattggcc aatctttgtt ctaaattgct aataaacgac      480
catttccgtc aattctcctt ggttgcaaca gtctacccgt caaatgttta ctaatttata      540
agtgtgaagt tgaattatg aaagacgaaa tcgtattaaa aattcacaag aataaacaac      600
tccatagatt ttcaaaaaaa cagtcacgag aaaaaaacca cagtccgttt gtctgctctt      660
ctagttttta ttatttttct attaatagtt ttttgttatt tcgagaataa aatttgaacg      720
atgtccgaac cacaaaagcc gagccgataa atcctaagcc gagcctaact ttagccgtaa      780
ccatcagtca cggctcccgg gctaattcat ttgaaccgaa tcataatcaa cggtttagat      840
caaactcaaa aaaatctaac ggcaacatag acgcgtcggt gagctaaaaa gagtgtgaaa      900
gccaggtcac catagcattg tctctcccag attttttatt tgggaaataa tagaagaaat      960
agaaaaaaat aaaagagtga gaaaaatcgt agaagcttgg tttcggattc aacgctataa     1020
ataaaaccac tctcgttgct gattcc                                          1046
```

<210> SEQ ID NO 46
<211> LENGTH: 1618
<212> TYPE: DNA
<213> ORGANISM: artificial sequence
<220> FEATURE:
<221> NAME/KEY: misc_feature
<222> LOCATION: (1)..(1618)
<223> OTHER INFORMATION: Chimeric promoter of linked AtAct7 enhancer and
      NteIF4A10 promoter

<400> SEQUENCE: 46

```
aattggccaa tctttgttct aaattgctaa taaacgacca tttccgtcaa ttctccttgg       60
ttgcaacagt ctacccgtca aatgtttact aatttataag tgtgaagttt gaattatgaa      120
agacgaaatc gtattaaaaa ttcacaagaa taaacaactc catagatttt caaaaaaaca      180
gtcacgagaa aaaaccaca gtccgtttgt ctgctcttct agttttatt attttttctat      240 taatagtttt ttgttatttc gagaataaaa tttgaacgat gtccgaacca caaaagccga      300
```

```
gccgataaat cctaagccga gcctaacttt agccgtaacc atcagtcacg gctcccgggc    360
taattcattt gaaccgaatc ataatcaacg gtttagatca aactcaaaac aatctaacgg    420
caacatagac gcgtcggtga gctaaaaaga gtgtgaaagc caggtcacca tagcattgtc    480
tctcccagat ttttatttg ggaaataata gaagaaatag aaaaaaataa aagagtgaga    540
aaaatcgtag agctgtcggc cgcatcatgt atatttgtgc atatccatga aaatttgtgt    600
tatatatacg atatataatg tgatacacat aggcgtccat aaaagaattg tgttgtatac    660
acgatataca aagtgatata cagatgtcct taaaaatatg tgtgtgatat acattgatgt    720
acacaatatg caacgcgata tacacatgtc acagttggat tttaggtctg atgttttaca    780
tgaaatcagt ctaaatcact tctaatcttg ctcaaatttt gtatatagcc ccgtttaggt    840
attttcaacc aatttcactc acaccactcg ttcaatctaa ccaaaaaaaa gaagagagaa    900 gaaaacaaa gttgaaatga attttttctct cttagttttt gcttataatt tttctgatta    960
ccttttcacc ccactgattt ttttttgcata atttgcaagg attttttgcta aactatgaga   1020 gcgaagaaa agagatagaa gaagaaaata caaggagaga aaggggggagg gacgcagtga   1080 acaaaaaaag aagttagcgg cgaagagggg ggggggggg aagcagacgg tttgggggcca   1140 attgtttgag agagaatata taagagagta gttttttag gatttggcta tataatgtca   1200
attttttggg gctatcttt cctaacctaa tataagacta aaaaattgtc aattcctgtt   1260
atgtgttatc acctggtgcc attttctcat agttatacat atagtgaaag gaaaagaggg   1320
tattagtgcc aatttttgtaa agaggttaga cctaaattag gcccaagagg cccaatagaa   1380
aatctagccc tcaatttgt ggaatccacg tcaccgactt cttgcattac cacccgaagc   1440
ggctccgtat tgatcctgta actcccaatt tcgggtcaaa ataggaattt caaatacaga   1500
agccaaaaaa aaaggaaag taatccaaaa cagtattcag aaagaccata aaaaaacact   1560
agtctcaatc cttctctttt cctctttcct gaactcctgc ggcgtagatc cgaggagt    1618
```

<210> SEQ ID NO 47
<211> LENGTH: 1039
<212> TYPE: DNA
<213> ORGANISM: artificial sequence
<220> FEATURE:
<221> NAME/KEY: misc_feature
<222> LOCATION: (1)..(1039)
<223> OTHER INFORMATION: Chimeric promoter of linked Act7 enhancer and
    AtTsf1 promoter

<400> SEQUENCE: 47

```
aattggccaa tctttgttct aaattgctaa taaacgacca tttccgtcaa ttctccttgg     60
ttgcaacagt ctacccgtca aatgtttact aatttataag tgtgaagttt gaattatgaa    120
agacgaaatc gtattaaaaa ttcacaagaa taaacaactc catagatttt caaaaaaaca    180
gtcacgagaa aaaaccaca gtccgtttgt ctgctcttct agttttttatt attttctat    240 taatagttttt ttgttattc gagaataaaa tttgaacgat gtccgaacca caaaagccga    300
gccgataaat cctaagccga gcctaacttt agccgtaacc atcagtcacg gctcccgggc    360
taattcattt gaaccgaatc ataatcaacg gtttagatca aactcaaaac aatctaacgg    420
caacatagac gcgtcggtga gctaaaaaga gtgtgaaagc caggtcacca tagcattgtc    480
tctcccagat ttttatttg ggaaataata gaagaaatag aaaaaaataa aagagtgaga    540
aaaatcgtag agcggccgcg gaagtttctc tcttgaggga ggttgctcgt ggaatgggac    600
acatatggtt gttataataa accatttcca ttgtcatgag attttgaggt taatatatac    660
```

```
tttacttgtt cattattttta tttggtgttt gaataaatga tataaatggc tcttgataat    720
ctgcattcat tgagatatca aatatttact ctagagaaga gtgtcatata gattgatggt    780
ccacaatcaa tgaaattttt gggagacgaa catgtataac catttgcttg aataaccttg    840
attaaaaggt gtgattaaat gatgtttgta acatgtagta ctaaacattc ataaaacaca    900
accaacccaa gaggtattga gtattcacgg ctaaacaggg gcataatggt aatttaaaga    960
atgatattat tttatgttaa accctaagct tggtttcgga ttcaacgcta taaataaaac   1020
cactctcgtt gctgattcc                                                1039
```

<210> SEQ ID NO 48
<211> LENGTH: 600
<212> TYPE: DNA
<213> ORGANISM: Arabidopsis thaliana

<400> SEQUENCE: 48

```
actagtcaac aattggccaa tctttgttct aaattgctaa taaacgacca tttccgtcaa     60
ttctccttgg ttgcaacagt ctacccgtca aatgtttact aatttataag tgtgaagttt    120
gaattatgaa agacgaaatc gtattaaaaa ttcacaagaa taaacaactc catagatttt    180
caaaaaaaca gtcacgagaa aaaaaccaca gtccgtttgt ctgctcttct agttttttatt   240 atttttctat taatagtttt tgttattttc gagaataaaa tttgaacgat gtccgaacca    300
caaaagccga gccgataaat cctaagccga gcctaacttt agccgtaacc atcagtcacg    360
gctcccgggc taattcattt gaaccgaatc ataatcaacg gtttagatca aactcaaaac    420
aatctaacgg caacatagac gcgtcggtga gctaaaaaga gtgtgaaagc caggtcacca    480
tagcattgtc tctcccagat tttttatttg ggaaataata gaagaaatag aaaaaaataa    540
aagagtgaga aaaatcgtag agctatatat tcgcacatgt actcgtttcg ctttccttag    600
```

<210> SEQ ID NO 49
<211> LENGTH: 480
<212> TYPE: DNA
<213> ORGANISM: Arabidopsis thaliana

<400> SEQUENCE: 49

```
gagagtttct ctcttgaggg aggttgctcg tggaatggga cacatatggt tgttataata     60
aaccatttcc attgtcatga gattttgagg ttaatatata ctttacttgt tcattatttt    120
atttggtgtt tgaataaatg atataaatgg ctcttgataa tctgcattca ttgagatatc    180
aaatatttac tctagagaag agtgtcatat agattgatgg tccacaatca atgaaatttt    240
tgggagacga acatgtataa ccatttgctt gaataacctt aattaaaagg tgtgattaaa    300
tgatgtttgt aacatgtagt actaaacatt cataaaacac aaccaaccca agaggtattg    360
agtattcacg gctaaacagg ggcataatgg taatttaaag aatgatatta ttttatgtta    420
aaccctaagc ttggtttcgg attcaacgct ataaataaaa ccactctcgt tgctgattcc    480
```

<210> SEQ ID NO 50
<211> LENGTH: 1054
<212> TYPE: DNA
<213> ORGANISM: Nicotiana tabacum

<400> SEQUENCE: 50

```
atcatgtata tttgtgcata tccatgaaaa tttgtgttat atatacgata tataatgtga     60
tacacatagg cgtccataaa agaattgtgt tgtatacacg atatacaaag tgatatacag    120
```

```
atgtccttaa aaatatgtgt gtgatataca ttgatgtaca caatatgcaa cgcgatatac      180
acatgtcaca gttggatttt aggtctgatg ttttacatga aatcagtcta aatcacttct      240
aatcttgctc aaattttgta tatagccccg tttaggtatt tcaaccaat ttcactcaca       300 ccactcgttc aatctaacca aaaaaaagaa gagagaagaa aaacaaagtt gaaatgaatt      360
tttctctctt agttttttgct tataattttt ctgattacct tttcaccca ctgattttttt    420 ttgcataatt tgcaaggatt tttgctaaac tatgagagcg aaagaaaaga gatgaagaa      480 gaaatacaag gagagaaagg gggagggacg cagtgaacaa aaaagaagt tagcggcgaa      540 gaggggggg gggggaagc agacggtttg gggccaattg tttgagagag aatatataag       600
agagtagttt ttttaggatt tggctatata atgtcaattt tttggggcta tcttttccta    660
acctaatata agactaaaaa attgtcaatt cctgttatgt gttatcacct ggtgccattt     720
tctcatagtt atacatatag tgaaaggaaa agagggtatt agtgccaatt ttgtaaagag     780
gttagaccta aattaggccc aagaggccca atagaaaatc tagccctcaa ttttgtggaa    840
tccacgtcac cgacttcttg cattaccacc cgaagcggct ccgtattgat cctgtaactc     900
ccaatttcgg gtcaaaatag gaatttcaaa tacagaagcc aaaaaaaaaa ggaaagtaat     960
ccaaaacagt attcagaaag accataaaaa aacactagtc tcaatctttc tcttttcctc    1020
tttcctgaac tcctgcggcg tagatccgag gagt                                 1054

<210> SEQ ID NO 51
<211> LENGTH: 609
<212> TYPE: DNA
<213> ORGANISM: Arabidopsis thaliana

<400> SEQUENCE: 51
atctctgagg taagcgttaa cgtacccctta gatcgttctt tttctttttc gtctgctgat     60
cgttgctcat attatttcga tgattgttgg attcgatgct cttttgttgat tgatcgttct   120 gaaaattctg atctgttgtt tagatttttat cgattgttaa tatcaacgtt tcactacttc   180
taaacgataa tttattcatg aaactatttt cccattctga tcgatcttgt tttgagattt    240
taatttgttc gattgattgt tggttggtgg atctatatac gagtgaactt gttgatttgc    300
gtatttaaga tgtatgtcga tttgaattgt gattgggtaa ttctggagta gcataacaaa   360
tccagtgttc ccttttttcta agggtaattc tcggattgtt tgctttatat ctcttgaaat  420
tgccgatttg attgaattta gctcgcttag ctcagatgat agagcaccac aattttttgtg 480 gtagaaatcg gtttgactcc gatagcggct ttttactatg attgttttgt gttaaagatg   540
attttcataa tggttatata tgtctactgt ttttattgat tcaatatttg attgttcttt  600
tttttgcag                                                            609

<210> SEQ ID NO 52
<211> LENGTH: 892
<212> TYPE: DNA
<213> ORGANISM: Nicotiana tabacum

<400> SEQUENCE: 52
gttagctatg ttttttttcc ctttaatatt ttaatgtatt tcttgtaata tttgtttgtg      60
tattgaagat tgaatcttga tgattgattg ttggtctgac tacagctggg ttttgtgtta    120
tgtaactatt tttaactatt ttggatagag gtctgtttga tgtgatgttc ttgattataa    180
aaataccatc ctactttgtt atctcatatc tggttggaac atgagcaatt tcatttctcc    240
tagttcttga attaaaaacc tgaaagtatt gtgcaaaaag atgctaggaa tgagactatc    300
```

-continued

```
attgttttga tgcaatatgt tcttttaagt aataggtgtt ttgtaagaag tctacgcagt    360
tctggatgta ttttactact cgggaaaact ggatagttgg atacttatta tgtataggaa    420
gtaaatgtgg ggattataat gcctttctct gccatctgct ctttgtattt tgtgtaaagc    480
ttggcatgcc tctcgtcaga tagccatcgc taccgtacat tctttaaga atgaagcact     540 tagacacttg ctcgtttctg cctttgtcac attgacccag catcatataa tctgaaagat    600
tggttagcag ttggctgcta tttaacttgt atgttaaaac aattgatttt catgtgtatc    660
tcctcctttt gtgctttgtg cttcttcata aaagaaagaa aacatacatt cggttgtgct    720
ctcctccttt ttcaatggta gagaggaaga acagataatt ttattgctgc tgtaggtatt    780
tgacatctgt gatattttca tagtaaggtt ttgtttttc ctttttattt agttcaagat    840
tgtttcatga atttccataa gcgtaatacc atagttcttt tatttgctac ag           892
```